(12) United States Patent
Schonbeck et al.

(10) Patent No.: US 9,687,580 B2
(45) Date of Patent: Jun. 27, 2017

(54) ABSORBENT ARTICLES COMPRISING STRETCH LAMINATES

(71) Applicant: The Procter & Gamble Company, Cincinnati, OH (US)

(72) Inventors: Marcus Schonbeck, Versmold (DE); Henner Sollmann, Gronau (DE); Georg Baldauf, Laer (DE); Urmish Popatlal Dalal, Milford, OH (US); Miguel Alberto Herrera, Loveland, OH (US); Erica Lynne Locke, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 37 days.

(21) Appl. No.: 14/265,436

(22) Filed: Apr. 30, 2014

(65) Prior Publication Data

US 2014/0330236 A1    Nov. 6, 2014

Related U.S. Application Data

(60) Provisional application No. 61/819,129, filed on May 3, 2013, provisional application No. 61/896,804, filed on Oct. 29, 2013.

(51) Int. Cl.
*A61L 15/24*    (2006.01)
*A61F 13/49*    (2006.01)

(52) U.S. Cl.
CPC .......... *A61L 15/24* (2013.01); *A61F 13/4902* (2013.01); *A61F 13/49015* (2013.01); *A61F 13/49019* (2013.01)

(58) Field of Classification Search
CPC .......... A61F 13/49015; A61F 13/49019; A61F 13/4902; A61F 13/49014; A61F 2013/49022; A61F 2013/49036; A61F 13/4963; A61L 15/24
See application file for complete search history.

(56) References Cited

U.S. PATENT DOCUMENTS

| | | |
|---|---|---|
| 3,848,594 A | 11/1974 | Buell |
| 4,116,892 A | 9/1978 | Schwarz |
| 4,515,595 A | 5/1985 | Kievit et al. |
| 4,662,875 A | 5/1987 | Hirotsu et al. |
| 4,699,622 A | 10/1987 | Toussant et al. |
| 4,710,189 A | 12/1987 | Lash |

(Continued)

OTHER PUBLICATIONS

PCT International Search Report, mailed Aug. 27, 2014 (9 pages).

(Continued)

*Primary Examiner* — Peter S Vasat
(74) *Attorney, Agent, or Firm* — Andrew J. Mueller; Wednesday G. Shipp

(57) ABSTRACT

An absorbent article includes a chassis comprising a topsheet, a backsheet, and an absorbent core disposed between the topsheet and the backsheet, and at least one elastically elongatable panel joined to the chassis. The elastically elongatable panel includes a stretch laminate that has at least one cover layer and an elastomeric film attached to the cover layer, the elastomeric film having two surfaces and a skin on at least one of the surfaces. The stretch laminate has at least one anchoring zone and at least one stretch zone and the skin that is located in the anchoring zone has a plurality of wrinkles.

20 Claims, 12 Drawing Sheets

(56) References Cited

U.S. PATENT DOCUMENTS

| | | |
|---|---|---|
| 4,834,741 A | 5/1989 | Sabee |
| 4,846,815 A | 7/1989 | Scripps |
| 4,892,536 A | 1/1990 | DesMarais et al. |
| 4,894,060 A | 1/1990 | Nestegard |
| 4,946,527 A | 8/1990 | Battrell |
| 4,990,147 A | 2/1991 | Freeland |
| 5,037,416 A | 8/1991 | Allen et al. |
| 5,143,679 A | 9/1992 | Weber et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,269,775 A | 12/1993 | Freeland et al. |
| 5,422,172 A | 6/1995 | Wu |
| 5,518,801 A | 5/1996 | Chappell et al. |
| 5,691,034 A | 11/1997 | Krueger et al. |
| 6,310,154 B1 | 10/2001 | Babcock et al. |
| 6,428,526 B1 | 8/2002 | Heindel et al. |
| 6,432,098 B1 | 8/2002 | Kline et al. |
| 6,713,159 B1 * | 3/2004 | Blenke et al. ............ 428/195.1 |
| 6,905,488 B2 | 6/2005 | Olson |
| 2005/0222546 A1 | 10/2005 | Vargo et al. |
| 2006/0149209 A1 * | 7/2006 | Malchow et al. ............ 604/389 |
| 2007/0003764 A1 * | 1/2007 | Muslet et al. ............ 428/411.1 |
| 2009/0264844 A1 * | 10/2009 | Autran et al. ................ 604/365 |
| 2010/0104830 A1 | 4/2010 | Jaeger et al. |
| 2011/0189495 A1 * | 8/2011 | Pip ................ 428/483 |
| 2014/0329053 A1 * | 11/2014 | Baldauf et al. ............... 428/152 |

OTHER PUBLICATIONS

U.S. Appl. No. 14/265,498, filed Apr. 30, 2014, Marcus Schonbeck et al.

U.S. Appl. No. 14/265,629, filed Apr. 30, 2014, Marcus Sehonbeek et al.

U.S. Appl. No. 14/265,651, filed Apr. 30, 2014, Marcus Schonbeck et al.

U.S. Appl. No. 14/265,673, filed Apr. 30, 2014, Marcus Sehonbeek et al.

U.S. Appl. No. 14/265,714, filed Apr. 30, 2014, Marcus Schonbeck et al.

* cited by examiner

ABSORBENT ARTICLES COMPRISING STRETCH LAMINATES

FIELD OF THE INVENTION

The present disclosure generally relates to stretch laminates and absorbent articles, such as diapers, pants, or the like, made using such stretch laminates.

BACKGROUND OF THE INVENTION

Disposable absorbent articles, such as diapers, are designed to contain bodily wastes and prevent soiling of the wearer's clothing and/or other items (e.g., a bed, a chair, a blanket, etc.). The fit of the article to the wearer's body is important in ensuring that these wastes are contained. Such articles are also designed to be cost-effective, and therefore manufacturers generally make the articles applicable for use by individuals with a wide range of body types. Accordingly, new and improved disposable absorbent articles that both conform to a wide range of body types and fit snuggly to the user to contain wastes and limit leakage are of continued interest.

One way in which manufacturers attempt to balance the competing interests of proper fit and variation in body type is through the use of expandable materials. One such group of materials is known as stretch laminates. As the name suggests, these materials are actually composites of individual components that are laminated together, through the use of an adhesive, for example. A typical stretch laminate will attempt to combine one or more layers of cover material with one or more layers or strands of an elastomeric material.

Complications arise in that stretch laminates are notoriously difficult and expensive to manufacture. Considerable effort has gone into proposing new types of stretch laminates and new methods for the fabrication of stretch laminates. In particular, a considerable number of patents discuss the difficulties of fabricating these laminates, and the significant and extensive steps that must be undertaken to prepare these laminates. Thus, there is a continuing need to provide new stretch laminates, new methods of fabricating better performing and/or cheaper stretch laminates, and new absorbent articles that comprise such stretch laminates.

SUMMARY OF THE INVENTION

In one aspect, an absorbent article includes i) a chassis comprising a topsheet, a backsheet, and an absorbent core disposed between the topsheet and the backsheet and ii) at least one elastically elongatable panel joined to the chassis. The elastically elongatable panel includes a stretch laminate that has at least one cover layer and an elastomeric film attached to the cover layer. The elastomeric film has two surfaces and a skin on at least one of the surfaces. The stretch laminate has at least one anchoring zone and at least one stretch zone, and the skin that is located in the anchoring zone has a plurality of wrinkles.

In another aspect, an absorbent article includes i) a chassis comprising a topsheet, a backsheet, and an absorbent core disposed between the topsheet and the backsheet and ii) at least one elastically elongatable panel joined to the chassis. The elastically elongatable panel includes a stretch laminate that has a first cover layer, a second cover layer, and an elastomeric film disposed between the first cover layer and the second cover layer. The elastomeric film has a first skin on a first surface closest to the first cover layer and a second skin on a second surface closest to the second cover layer. The stretch laminate has at least one anchoring zone and at least one stretch zone, and the first skin and the second skin that are located in the anchoring zone each have a plurality of wrinkles.

Additional aspects of the disclosure are defined by the claims of this patent.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Definitions

Figure 1A:
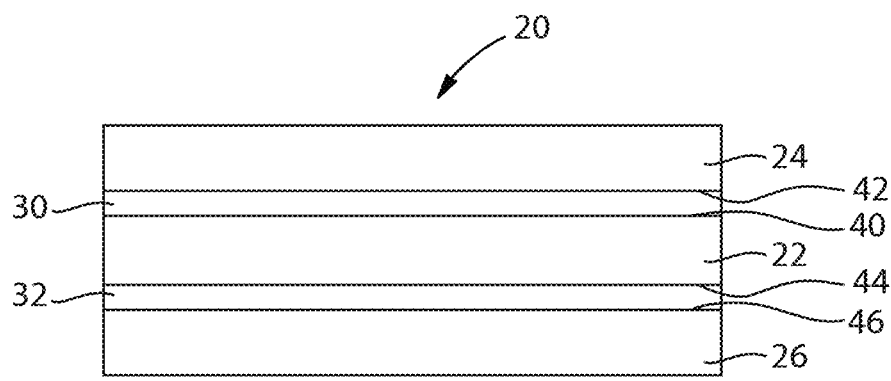
FIG. 1A is a cross-sectional view of a first embodiment of a stretch laminate according to the present disclosure.

As used herein, the following terms have the following meanings:

The term "absorbent article" refers to a device that absorbs and contains liquid, and more specifically, refers to a device that is placed against or in proximity to the body of the wearer to absorb and contain the various wastes/exudates discharged from the body.

The terms "activated" and "pre-activated" refer to a process of mechanically deforming a material in order to increase the extensibility of at least a portion of the material. A material may be activated or pre-activated by, for example, incrementally stretching the material in at least one direction.

The terms "adhesively bonded" or "adhesively laminated" refer to a laminate wherein an adhesive is used to bond an elastomeric material to at least one cover layer.

The term "attached" refers to elements being connected or united by fastening, adhering, bonding, or by any other method suitable for connecting the elements together and to their constituent materials. Many suitable methods for attaching elements together are well-known, including adhesive bonding, pressure bonding, thermal bonding, ultrasonic bonding, mechanical fastening, etc. Such attachment methods may be used to attach elements together over a particular area either continuously or intermittently.

The term "diaper" refers to an absorbent article generally worn by infants and incontinent persons about the lower torso and having the general form of a sheet, different portions of which are fastened together to encircle the waist and the legs of the wearer.

The term "disposable" refers to absorbent articles that generally are not intended to be laundered or otherwise restored or reused as absorbent articles, i.e., they are intended to be discarded after a single use and, preferably, to be recycled, composted or otherwise disposed of in an environmentally compatible manner.

The term "disposed" is used to mean that an element(s) is formed (joined and positioned) in a particular place or position as a unitary structure with other elements or as a separate element joined to another element.

The term "extensible" refers to the property of a material, wherein: when a biasing force is applied to the material, the material can be extended to an elongated length of at least 110% of its original relaxed length (i.e., can extend 10%), without a rupture or breakage that renders the material unusable for its intended purpose. A material that does not meet this definition is considered inextensible. In some embodiments, an extensible material may be able to be extended to an elongated length of 125% or more of its original relaxed length without rupture or breakage that renders the material unusable for its intended purpose. An extensible material may or may not exhibit recovery after application of a biasing force.

Throughout the present disclosure, an extensible material is considered to be "elastically extensible" if, when a biasing force is applied to the material, the material can be extended to an elongated length of at least 110% of its original relaxed length (i.e., can extend 10%), without rupture or breakage which renders the material unusable for its intended purpose, and when the force is removed from the material, the material recovers at least 40% of its elongation. In various examples, when the force is removed from an elastically extensible material, the material may recover at least 60%, or at least 80%, of its elongation.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower" and "top" and "bottom", respectively.

The term "joined" refers to configurations whereby an element is directly secured to another element by attaching the element directly to the other element, and configurations whereby an element is indirectly secured to another element by attaching the element to intermediate member(s) which in turn are attached to the other element.

The term "lateral" or "transverse" refers to a direction running at a 90 degree angle to the longitudinal direction and includes directions within =45° of the lateral direction.

The term "longitudinal" refers to a direction running parallel to the maximum linear dimension of the article and includes directions within ±45° of the longitudinal direction.

The term "pant" or "pants" refers to an absorbent article generally worn by infants and incontinent persons about the lower torso and having the general form of a pair of short pants that can be applied or removed from the wearer without unfastening. A pant may be placed in position on the wearer by inserting the wearer's legs into the leg openings and sliding the pant into position about the wearer's lower torso. While the term "pant" is used herein, pants are also commonly referred to as "closed diapers", "prefastened diapers", "pull-on diapers", "training pants" and "diaper-pants".

The term "recovery" refers to ability of a material to return to its original size after it has been stretched.

The term "refastenable" refers to the property of two elements being capable of releasable attachment, separation, and subsequent releasable reattachment without substantial permanent deformation or rupture.

The terms "releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

The "strain" or "percent strain" of a material is calculated by subtracting the original length from the stretched length, then dividing the result by the original length and multiplying by 100. The percent strain is described by the equation below:

$$\text{Percent Strain} = \% \text{ Strain} = \text{Strain} = 100 * [(L_s - L_0)/L_0]$$

where $L_0$ is the original length of the stretch laminate (or elastomeric film) at the beginning of the stretch step, and $L_s$ is the length of the stretched laminate (or elastomeric film)

at the end of the stretch step. A sample stretched from an original length of 10 mm to a length of 30 mm results in a strain of 200%. Strain can be calculated in a length direction, a width direction, or any direction there between.

The "set" or "percent set" of a material is calculated by subtracting an original length from a final length, then dividing the result by the original length and multiplying by 100. The percent set is described by the equation below:

$$\text{Percent Set} = \% \text{ Set} = \text{Set} = 100 * [(L_f - L_0)/L_0]$$

where $L_0$ is an original length of the stretch laminate (or elastomeric film) at the beginning of the stretch step, and $L_f$ is a length of the relaxed stretch laminate (or elastomeric film) after it is relaxed from the stretch step. A sample is stretched from an original length of 10 mm to a length of 30 mm. Upon relaxing (removal of stress), the sample returns to 15 mm. This results in a set of 50%. Set can be calculated in a length direction, a width direction, or any direction there between.

The term "wrinkle" refers to a small fold, ridge or crease.

Stretch Laminate

Figure 1B:
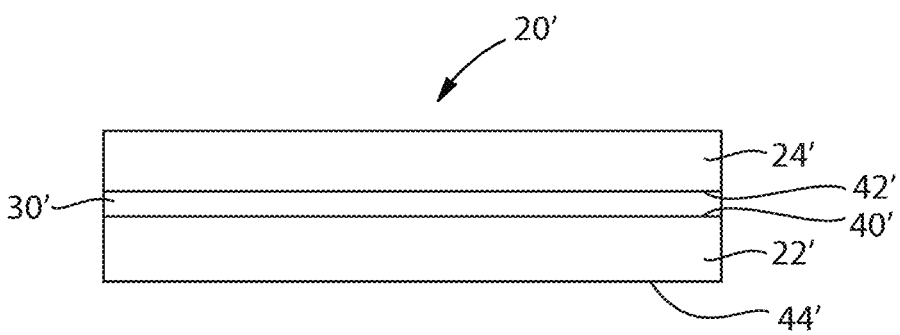
FIG. 1B is a cross-sectional view of a second embodiment a stretch laminate according to the present disclosure.

FIG. 1A illustrates an embodiment of a stretch laminate 20 according to the present disclosure. According to this embodiment, laminate 20 may include three layers: an elastomeric film 22, a first cover layer 24, and a second cover layer 26. However, according to other embodiments (as depicted in FIG. 1B), a laminate 20' may only include two layers: an elastomeric film 22' and a cover layer 24'. Although the following description will refer to the specific reference numbers in FIG. 1A, the prime versions of those numbers relating to the two layer embodiment of FIG. 1B are also intended to be considered by the reader. For example, when the description refers to "elastomeric film 22 and first cover layer 24 of stretch laminate 20", it is intended that the reader also consider the same description for "elastomeric film 22' and cover layer 24' of stretch laminate 20'."

Elastomeric film 22 and cover layers 24, 26 may be attached to each other. For example, an adhesive 30, 32 may be disposed between layers 22, 24, 26. As will be recognized, adhesive 30 may be initially disposed either on a first surface 40 of elastomeric film 22 or a surface 42 of cover layer 24, and adhesive 32 may similarly be initially disposed either on a second surface 44 of elastomeric film 22 or a surface 46 of cover layer 26. As assembled, adhesive 30 attaches surface 40 (and thus elastomeric film 22) to surface 42 (and thus cover layer 24), and adhesive 32 attaches surface 44 (and thus elastomeric film 22) to surface 46 (and thus cover layer 26).

While the layers 22, 24, 26 appear to overlie each other completely, this need not be the case in all embodiments. For example, cover layers 24, 26 may extend beyond elastomeric film 22, and may be attached one to the other where the layers 24, 26 extend beyond elastomeric film 22; alternatively, cover layers 24, 26 may not extend to the limits of elastomeric film 22. Also, while adhesive 30, 32 appears as a continuous layer in FIGS. 1A and 1B, the adhesive may be applied as a continuous layer or in a discontinuous pattern (such as a pattern of lines, spirals, or spots). Accordingly, the bonding can be the full width of stretch laminate 20 or a partial width of the laminate (e.g., intermittent or zone bonding). Further, alternative attachment mechanisms may include heat bonding, pressure bonding, ultrasonic bonding, dynamic mechanical bonding, or any other suitable attachment mechanism or combination of these attachment mechanisms.

Elastomeric film 22 of stretch laminate 20 includes a single layer or multiple layer material that is elastically extensible. The elastically extensible material may be between about 10 μm and about 100 μm, or between about 20 μm and about 60 μm, or between about 30 μm and about 50 μm, or in some embodiments, about 40 μm, in thickness. The elastically extensible material may comprise an elastomeric polyolefin, and in some embodiments, a polyolefin (POE) blown film. Non-limiting examples of useful elastically extensible materials include propylene based homopolymers or co-polymers, or ethylene based homopolymers or co-polymers selected from the group consisting of: an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene tri-block copolymer, an isotactic polypropylene block region-irregular polypropylene block isotactic polypropylene tri-block copolymer, a polyethylene random (ethylene/olefin) copolymer block copolymer, a reactor blend polypropylene, a very low density polypropylene, a metallocene polypropylene, metallocene polyethylene, and combinations thereof. Additional non-limiting examples of useful elastically extensible materials include styrene-isoprene-styrene block copolymers, styrene-butadiene-styrene block copolymers, styrene-ethylene-butylene-styrene block copolymers, polyurethanes, ethylene copolymers, polyether block amides, and combinations thereof.

The elastically extensible material may comprise modifying resins. Such modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; natural and modified rosins and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. Modifying resins may also include alicyclic terpenes, hydrocarbon resins, cycloaliphatic resins, poly-beta-pinene, terpene phenolic resins, and combinations thereof. Useful C5 hydrocarbon resins and C9 hydrocarbon resins are disclosed in U.S. Pat. No. 6,310,154.

The elastically extensible material may comprise a variety of additives. Suitable additives including, but not limited to, stabilizers, antioxidants, and bacteriostats may be employed to prevent thermal, oxidative, and bio-chemical degradation of the elastically extensible material. Additives may account for about 0.01% to about 60% of the total weight of the elastically extensible material. In other embodiments, the composition comprises from about 0.01% to about 25%. In other suitable embodiments, the elastically extensible material comprises from about 0.01% to about 10% by weight, of additives.

The elastically extensible material may comprise various stabilizers and antioxidants that are well known in the art and include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Proprietary commercial stabilizers and/or antioxidants are available under a number of trade names including a variety of Wingstay®, Tinuvin® and Irganox® products.

The elastically extensible material may comprise various bacteriostats that are known in the art. Examples of suitable bacteriostats include benzoates, phenols, aldehydes, halogen containing compounds, nitrogen compounds, and metal-containing compounds such as mercurials, zinc compounds and tin compounds. A representative example is available under the trade designation Irgasan Pa. from Ciba Specialty Chemical Corporation of Tarrytown, N.Y.

The elastically extensible material may comprise viscosity modifiers, processing aids, slip agents or anti-block agents. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. Mineral oil may be used as a processing oil. Viscosity modifiers are also well known in the art. For example, petroleum derived waxes can be used to reduce the viscosity of the slow recovery elastomer in thermal processing. Suitable waxes include low number-average molecular weight (e.g., 0.6-6.0 kilo Daltons) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

Elastomeric film 22 also includes at least one skin disposed on the elastically extensible material, the skin forming at least one of the film's surfaces 40, 44. Such skin is an extensible material and provides an outer surface to elastomeric film 22 that has less tackiness than the underlying elastically extensible material. In some embodiments, the skin may also qualify as an elastically extensible material, but will be less elastic than the underlying elastically extensible material. Accordingly, when compared to the elastically extensible material, the skin will have less recovery from the same amount of extension. Or in other words, when compared to the elastically extensible material, the skin will have a higher percentage set from the same percentage strain. The skin may aid in elastomeric film 22 processablity and is between about 1 μm and about 10 μm, or between about 3 μm and about 7 μm, or in some embodiments, is about 5 μm, in thickness. In certain embodiments, the skin that overlays the elastically extensible material in elastomeric film 22 is a polyolefin. Non-limiting examples of useful skin materials include metallocene polyethylene, low density polyethylene, high density polyethylene, linear low density polyethylene, very low density polyethylene, a polypropylene homopolymer, a plastic random poly(propylene/olefin) copolymer, syndiotactic polypropylene, metallocene polypropylene, polybutene, an impact copolymer, a polyolefin wax, and combinations thereof.

Exemplary elastomeric films that are useful in the stretch laminates detailed herein (i.e., an elastically extensible material with at least one skin disposed on the surface of the elastically extensible material) include M18-1117 and M18-1361 elastomeric films commercially available from Clopay Corporation of Cincinnati, Ohio; K11-815 and CEX-826 elastomeric films commercially available from Tredegar Film Products of Richmond, Va.; and elastomeric films commercially available from Mondi Gronau GmbH of Gronau, Germany. These exemplary elastomeric films include a single layer of elastically extensible material with a skin disposed on both surfaces of the material. Referring to FIG. 1A, such exemplary elastomeric films would have a skin providing first surface 40 and a second skin providing second surface 44. However, other elastomeric films applicable to the stretch laminates detailed herein only need to have a skin that provides first surface 40 or second surface 44.

The cover layers 24, 26 may include a nonwoven material, including but not limited to, spun only or spun meltblown combinations, such as SM (spunbond meltblown), SMS (spunbond meltblown spunbond), SMMS (spunbond meltblown meltblown spunbond) nonwovens, SSMMS (spunbond spunbond meltblown meltblown spunbound), hydroentangled nonwovens and softbond nonwovens. The nonwoven materials may also include carded nonwovens, such as those specially designed and manufactured to be compatible with an activation (e.g., ring-rolling) process. One exemplary nonwoven material is a carded nonwoven made from a polypropylene homopolymer. The spunbounds may also be specially designed and/or manufactured to be compatible with an activation process. However, it is believed that through the use of the elastomeric film according to the present disclosure, greater flexibility in the design choices may be achieved. For example, spunbounds may be selected for applications where only carded nonwovens were used in the past, or thinner elastomeric films may be used with the carded nonwovens. Other improvements in design flexibility will also be recognized by the skilled practitioner. For example, in some embodiments, the cover layer(s) may be extensible nonwovens and may or may not need to undergo an activation process in order to impart extensibility to the stretch laminate.

The basis weight of the nonwoven material may be less than about 30 gsm. In fact, according to certain embodiments, the basis weight may be less than about 27 gsm. In other embodiments, the basis weight may be less than about 25 gsm. In still other embodiments, the nonwoven material may have a basis weight of less than about 24 gsm. The nonwoven materials may also include additives, such as, for example, $CaCO_3$. Woven or knitted fabrics may also be used as cover layers 24, 26 in embodiments of the stretch laminates detailed herein.

Adhesive 30, 32 may be selected from any adhesives known to provide suitable attachment between elastomeric film 22 and cover layers 24, 26. In some embodiments, the adhesive may be a hot melt adhesive with a basis weight of less than about 15 gsm. According to one embodiment, the adhesive may be H2031 adhesive commercially available from Bostik Inc. of Middleton, Mass. One characteristic of this adhesive is that, at 23° C., this adhesive has significant pressure-sensitive character useful for making a stretch laminate by hand. However, this adhesive is also suitable for use in fabricating stretch laminates from the elastomeric films and cover layers listed above using conventional stretch laminate manufacturing equipment, such equipment being well known in the art.

Elastomeric film 22 is mechanically pre-activated before attachment to at least one cover layer 24, 26. As further detailed in the STRETCH LAMINATE FABRICATION METHOD below, elastomeric film 22 may be pre-activated by being stretched transversely to its web direction by more than 50% (i.e., strain >50%). In some embodiments, an expansion by about 100% to about 500% occurs in relation to the starting width of elastomeric film 22. In alternate embodiments, elastomeric film 22 may be stretched in the web direction, stretched a direction other than the web direction or transverse to the web direction, or a combination of directions. The term "stretching" is to point to the fact that the expansion of elastomeric film 22 is not completely reversible and that a non-elastic fraction results in the film having a larger width following pre-activation (i.e., the elastomeric film does not have 100% recovery, and therefore has a percent set value). After expansion, elastomeric film 22 retracts and has a width that may be larger by about 10% to about 30% in relation to a starting width of the film. In other words, after the pre-activation expansion and retraction detailed below, elastomeric film 22 may exhibit a set of about 10% to about 30%.

In addition, because elastomeric film 22 includes both an elastically extensible material and at least one skin disposed on the elastically extensible material, and because these materials have different elasticity and recovery properties, the pre-activation process will physically alter these materials differently. During pre-activation, the skin and the elastically extensible material are similarly stretched (i.e., put under similar strain). However, after stretching, the skin and the elastically extensible material will retract and recover differently (i.e., have different set values). In comparison with the elastically extensible material, the skin is less elastic and therefore will have less recovery after stretching, a.k.a., a higher set value. The skin is also much thinner than the elastically extensible material, so when the thicker elastically extensible material retracts and recovers after pre-activation stretching, it will force the attached skin to retract with it. But because the skin cannot recover as much as the elastically extensible material, the skin buckles and wrinkles. Accordingly, the cross-sectional profile and the top view appearance of elastomeric film 22 are modified after a pre-activation process.

Figure 2:
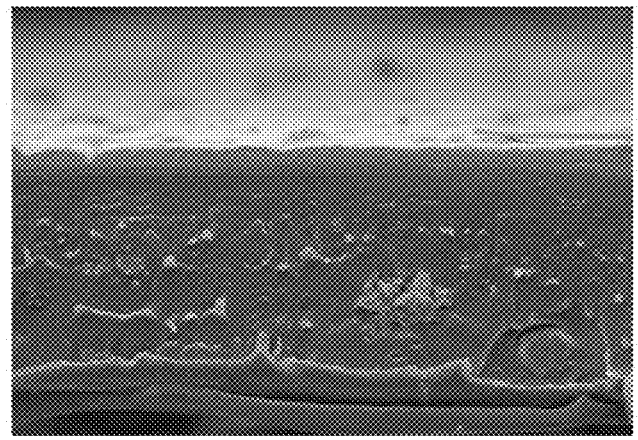
FIG. 2 is a SEM photomicrograph showing a cross-sectional view of a portion of an elastomeric film that has not been pre-activated.
Figure 3:
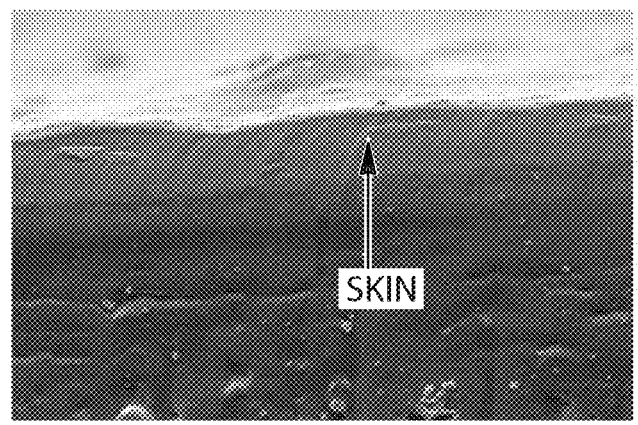
FIG. 3 is a magnified version of the SEM photomicrograph of FIG. 2.

FIGS. 2-5 are SEM photomicrographs of magnified cross-sections of elastomeric films. These SEM photomicrographs, as well as the other SEM photomicrographs included herein, were taken with a scanning electron microscope (Hitachi Model 3500). The information to calculate specific magnifications and distances is included in each individual SEM photomicrograph along the bottom of the frame. FIG. 2 is a SEM photomicrograph taken at approximately 900× magnification showing a cross-sectional view of a portion of an elastomeric film that has not been pre-activated. The skins are the thin strips of contrasting material at the top and the bottom of the cross-section, with the thicker elastically extensible material between the skins. The skin at the top of the cross-section is easier to discern due to the cross-section being cut cleaner in that region. Without pre-activation, the skins, and thus the outer surfaces of the elastomeric film, are substantially smooth in a cross-sectional view. FIG. 3 is a higher magnification image (approx. 3500× magnification) of the skin at the top of cross-section shown in the SEM photomicrograph of FIG. 2.

Figure 4:
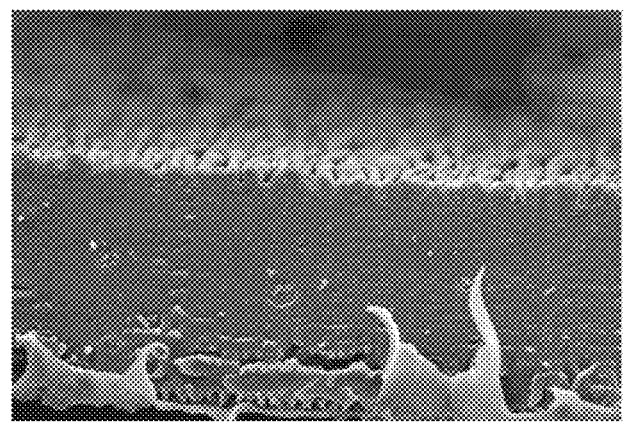
FIG. 4 is a SEM photomicrograph showing a cross-sectional view of a portion of a pre-activated elastomeric film.
Figure 5:
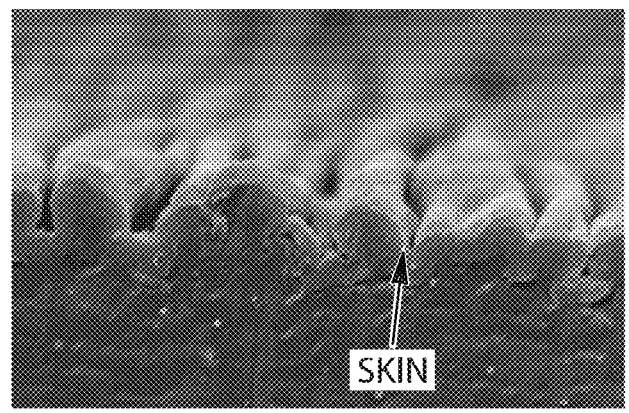
FIG. 5 is a magnified version of the SEM photomicrograph of FIG. 4.

FIG. 4 is a SEM photomicrograph taken at approximately 900× magnification showing a cross-sectional view of a portion of an elastomeric film that has been pre-activated. Again, the skins are the thin strips of contrasting material at the top and the bottom of the cross-section, with the thicker elastically extensible material between the skins. With pre-activation, the skins, and thus the outer surfaces of the elastomeric film, are wrinkled in a cross sectional view. FIG. 5 is a higher magnification image (approx. 3500× magnification) of the skin at the top off the cross-section shown in the SEM photomicrograph of FIG. 4.

FIGS. 4 and 5 show that after pre-activation, the skin of elastomeric film 22 includes a plurality of wrinkles having hills and furrows. For example, as shown in the non-limiting sample photographed in FIG. 5, there are approximately six hills and six furrows of varying size within the pictured approximately 35 μm of length taken along the cross-sectional profile of the pre-activated elastomeric film. This is in comparison to FIG. 3, in which there are no hills and no furrows within the pictured approximately 35 μm of length taken along the cross-sectional profile of an elastomeric film that was not pre-activated. However, as visible on the top surface of the elastomeric film shown in FIG. 3, one or more random hills and/or furrows may be present within a particular length of cross-sectional profile of an elastomeric film that was not pre-activated. These random hills and/or furrows are due to irregularities in the surface of the elastomeric film. Such random hills and/or furrows should not be confused with the hills and furrows of the plurality of wrinkles that are intentionally formed in an elastomeric film through a mechanical pre-activation process.

Figure 6:
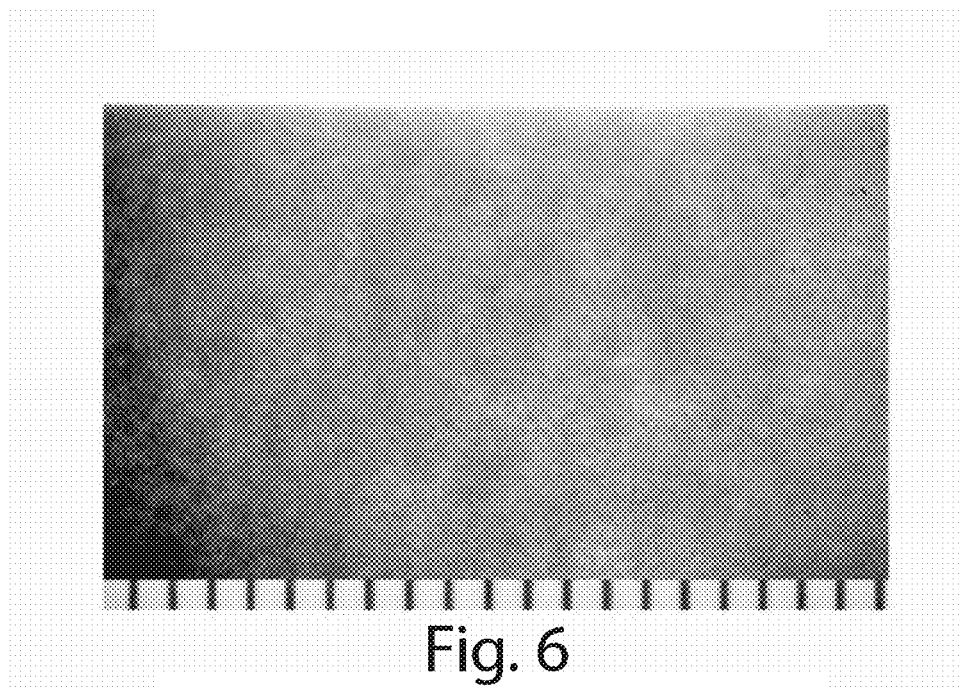
FIG. 6 is a transmitted light photomicrograph of a top view of a portion of an elastomeric film that has not been pre-activated.
Figure 7:
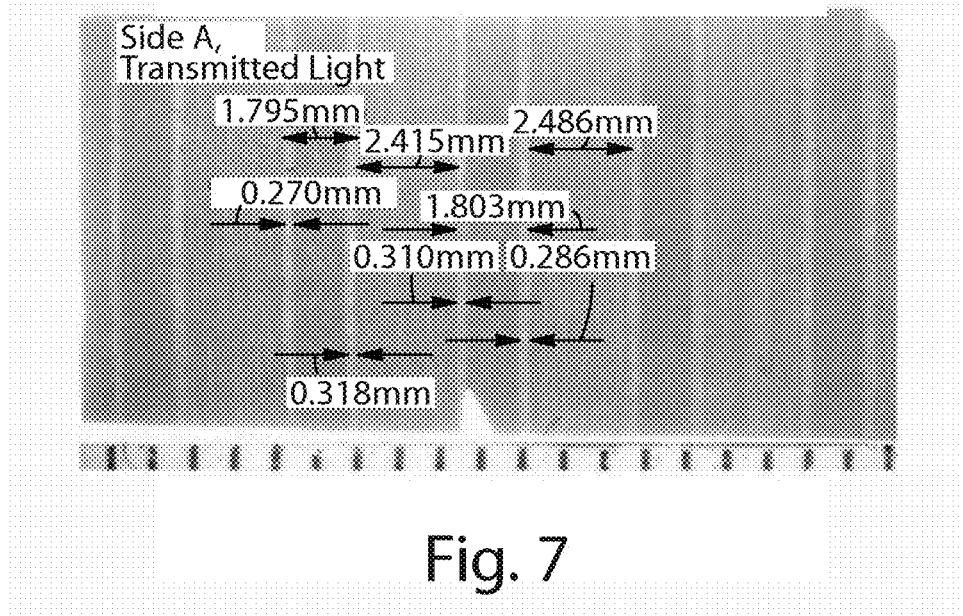
FIG. 7 is a transmitted light photomicrograph of a top view of a portion of a pre-activated elastomeric film.

FIGS. 6 and 7 are transmitted light photomicrographs of magnified top views of elastomeric films. The transmitted light photomicrographs were taken in color using a Nikon SMZ 1500 Stereo Light Microscope equipped with an Evolution Mp5C Digital camera with white light shining underneath the elastomeric film samples. The blue scale marks at the bottoms of FIGS. 6 and 7 are in millimeters. This scale can be used to calculate specific magnifications and distances in the transmitted light photomicrographs. FIG. 6 is a transmitted light photomicrograph showing a top view of a portion of an elastomeric film that has not been pre-activated. Without pre-activation, the viewable outer surface of the elastomeric film (i.e., the top view of the skin), has no discernible stripes and is uniform in appearance. FIG. 7 is a transmitted light photomicrograph showing a top view of a portion of an elastomeric film that has been pre-activated. With pre-activation, the top view of the skin includes a plurality of stripes in varying thicknesses that relate to the size and pitch of the intermeshing discs of the mechanical pre-activation means (as further detailed in the STRETCH LAMINATE FABRICATION METHOD below). The stripes, referred to herein as activation stripes, indicate zones in the pre-activated elastomeric film in which there was a particular range of stretching during the pre-activation process. For example, as shown in non-limiting sample photographed in FIG. 7, there are medium thickness darker blue stripes indicative of a heavier intensity skin wrinkling, large thickness light blue stripes indicative of medium intensity skin wrinkling, and thin white stripes indicative of lower intensity skin wrinkling.

In addition, after preactivation, but before utilizing elastomeric film 22 in the fabrication of stretch laminate 20, the film may optionally be printed with an image or motif that may show through the cover layers of the stretch laminate. The ink or other pigment utilized in printing will be deposited on the hills and into the furrows of the wrinkles of the pre-activated elastomeric film. Ink deposited onto the textured surface of a pre-activated elastomeric film allows for more contact surface area between the elastomeric film and the ink. Accordingly, when printing on a pre-activated elastomeric film, there is an image that is more strongly set on the film when compared to an image printed on the much smoother surface of an elastomeric film that has not been pre-activated.

Moreover, when stretch laminate 20 includes a pre-activated (and subsequently printed) elastomeric film that is mechanically activated (as further detailed in the STRETCH LAMINATE FABRICATION METHOD below), a non-distorted printed image on the film is evenly and reversibly stretched along with it. This is because before the image was printed on the pre-activated elastomeric film, a significant portion, or the entire, non-elastic fraction of elastomeric film 22 has already been removed in the pre-activation process.

In other words, the set had been removed from elastomeric film 22 before printing. Therefore, the printed image will not substantially distort further with the later activation of stretch laminate 20, or in additional stretching of the laminate by a user. In contrast, if an image or motif were printed on an elastomeric film that was not pre-activated, and that printed film was then used in fabricating a stretch laminate, and then the stretch laminate was mechanically activated, the desired image would be distorted in the final activated stretch laminate. This is because the set of the elastomeric film was not removed prior to the printing process, and such set would be removed from the elastomeric film in the mechanical activation of the fabricated stretch laminate, thus distorting the original printed image. Likewise, if an elastomeric film is printed and then subsequently preactivated, the set of the elastomeric film will not be removed prior to the printing process, and such set would be removed from the elastomeric film in the pre-activation process, thus distorting the original printed image.

And in another embodiment, a pre-activated elastomeric film may be stretched again during the printing of the film. The printed film is then relaxed and used in fabrication and activation of the stretch laminate. The resulting activated stretch laminate has an image or motif that is aesthetically pleasant when the stretch laminate is in a stretched condition during use (e.g., when a user stretches the stretch laminate in application or removal of an absorbent article).

Figure 8:
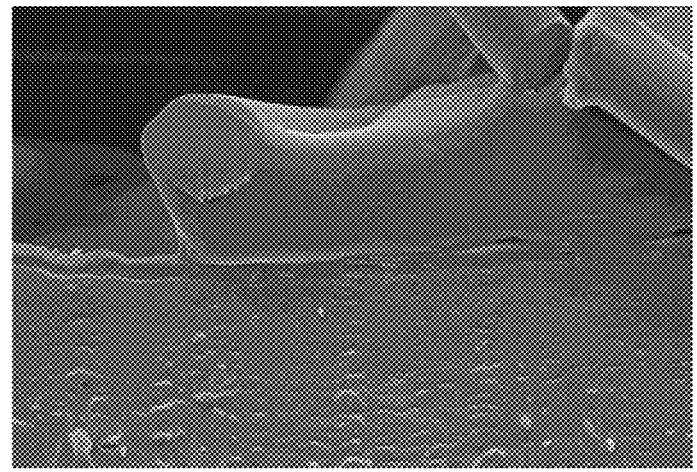
FIG. 8 is a SEM photomicrograph showing a cross-sectional view of a portion of a stretch laminate that includes an elastomeric film that has not been pre-activated.
Figure 9:
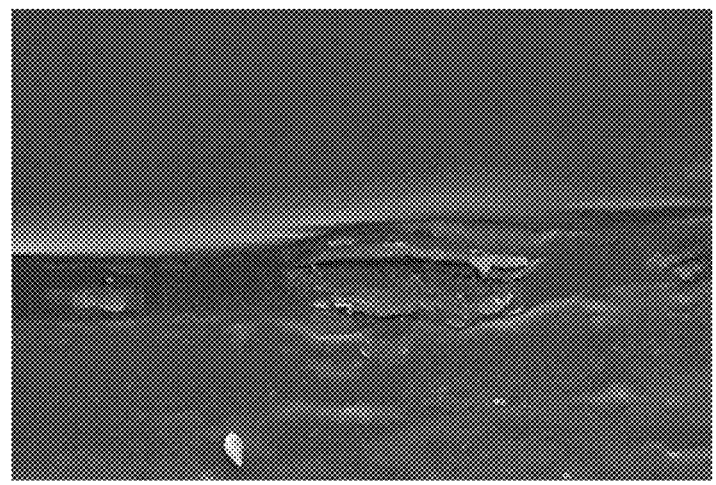
FIG. 9 is a magnified version of the SEM photomicrograph of FIG. 8.

In fabricating stretch laminate 20, cover layers 24, 26 are attached to elastomeric film 22 through the use of adhesives 30, 32. When utilizing an elastomeric film that has not been pre-activated, the adhesive has a relatively smooth surface in which to adhere. FIG. 8 is a SEM photomicrograph taken at approximately 900x magnification showing a cross-sectional view of a portion of a stretch laminate that includes an elastomeric film that has not been pre-activated. The skin is the thin contrasting strip of material running about midway through the photomicrograph, with the thicker elastically extensible material below the skin. Disposed on top of the skin is an adhesive, which is also attached to the cover layer. In this exemplary embodiment, the fibers of the cover layer are the large cylindrical objects at the top of the SEM photomicrograph. Without pre-activation, the skins, and thus the outer surfaces of the elastomeric film, are substantially smooth in a cross-sectional view. FIG. 9 is a higher magnification image (approx. 3500x magnification) of the interaction between the skin and glue as shown in the SEM photomicrograph of FIG. 8.

Figure 10:
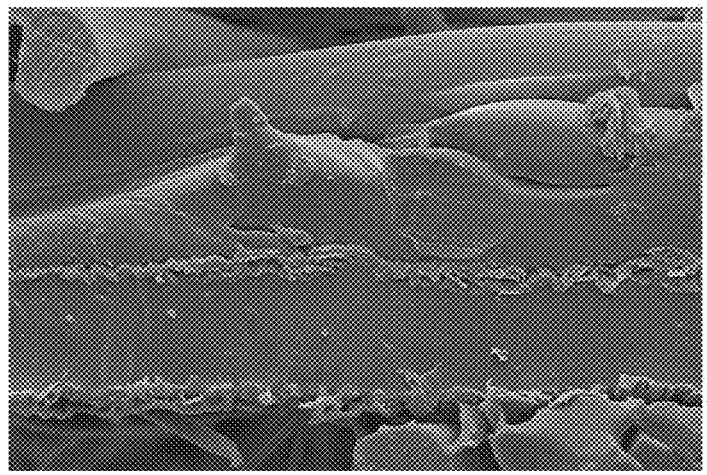
FIG. 10 is a SEM photomicrograph showing a cross-sectional view of a portion of a stretch laminate that includes an elastomeric film that has been pre-activated.
Figure 11:
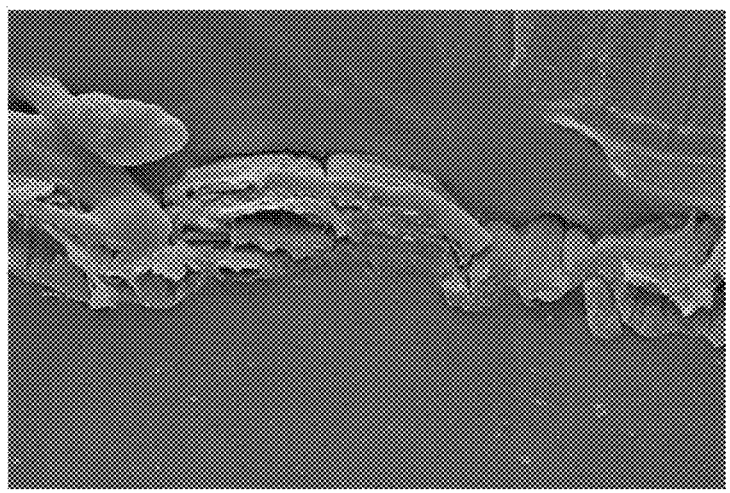
FIG. 11 is a magnified version of the SEM photomicrograph of FIG. 10.

FIG. 10 is a SEM photomicrograph taken at approximately 900x magnification showing a cross-sectional view of a portion of a stretch laminate that includes an elastomeric film that has been pre-activated. The skins are the contrasting strips of material running through the middle of the photomicrograph, with the thicker elastically extensible material between the skins. With pre-activation, the skins, and thus the outer surfaces of the elastomeric film, are wrinkled in a cross sectional view. Disposed on outer surfaces of the skin (i.e., the surfaces not contacting the elastically extensible material) is adhesive, which is also attached to the cover layer. In this exemplary embodiment, the fibers of the cover layer are the large cylindrical objects at the top and bottom of the SEM photomicrograph. The pre-activated elastomeric film includes a textured skin with wrinkles in a cross-sectional view. FIG. 11 is a higher magnification image (approx. 3500x magnification) of the skin at the top of the elastomeric film shown in the SEM photomicrograph of FIG. 10.

As previously shown in FIGS. 4 and 5, FIGS. 10 and 11 also illustrate that after pre-activation, the skin of elastomeric film 22 is textured and includes a plurality of wrinkles having hills and furrows. Adhesive 30, 32 that attaches elastomeric film 22 to cover layers 24, 26 may flow over the hills and into the furrows of the pre-activated elastomeric film. Accordingly, adhesive 30, 32 is disposed in the furrows of the skin of elastomeric film 22. This is in comparison to FIGS. 8 and 9, in which there are no furrows in the elastomeric film for the adhesive to flow into. Adhesive flowing into the furrows of a pre-activated elastomeric film allows for more contact surface area between the film and the adhesive, leading to a stronger bond between the cover layer and the film. Accordingly, when using the same amount of adhesive, there is a stronger bond (e.g., better creep resistance) between a pre-activated elastomeric film and a cover layer when compared to the bond between an elastomeric film that has not been pre-activated and a cover layer. Moreover, when employing a pre-activated elastomeric film, previous bond strengths between elastomeric films that were not pre-activated and a cover layer may be achievable with the use of less adhesive.

In embodiments of stretch laminates that include a elastomeric film that is pre-activated and subsequently printed, the ink or other pigment utilized in printing will be deposited on the hills and into the furrows of the wrinkles of the film. As detailed above, ink deposited onto the textured surface of a pre-activated elastomeric film will more strongly set on the film due to the additional contact surface area between the elastomeric film and the ink (in comparison to ink disposed on a elastomeric film that has not been pre-activated). Adhesive 30, 32 that attaches elastomeric film 22 to cover layers 24, 26 may also flow over the hills and into the furrows of the pre-activated elastomeric film. Accordingly, adhesive 30, 32 is disposed over the ink and/or in the furrows of the skin of pre-activated elastomeric film 22. And because the ink is more strongly set on the pre-activated elastomeric film, when using the same amount of adhesive, there is a stronger bond (e.g., better creep resistance) between a pre-activated (and subsequently printed) elastomeric film and a cover layer when compared to the bond strength between an printed elastomeric film that has not been pre-activated and a cover layer. Moreover, when employing a pre-activated (and subsequently printed) elastomeric film, previous bond strengths between printed elastomeric films that were not pre-activated and a cover layer may be achievable with the use of less adhesive.

In addition, pre-activating an elastomeric film also lowers the force needed to later stretch the film (versus a non-activated film). This helps the later mechanical activation of the stretch laminate (as further detailed in the STRETCH LAMINATE FABRICATION METHOD below) because the load required to activate a stretch laminate that is made with pre-activated film will be lower (versus a non-activated film).

Exemplary Ear Panel and Absorbent Article

Having thus described the stretch laminate above, the use of the stretch laminate in a side panel of an absorbent article is now detailed. Specifically, the exemplary embodiment below details an ear panel portion of a side panel that is fabricated from a stretch laminate detailed herein. In addition to use in side panels as detailed below, the stretch laminates described herein may also be used in other portions of the side panels of pants diapers and taped diapers. Further, while use of the stretch laminate is suggested in regard to certain regions of the absorbent article, it will be recognized that the stretch laminate may be used in other regions as well.

Figure 12:
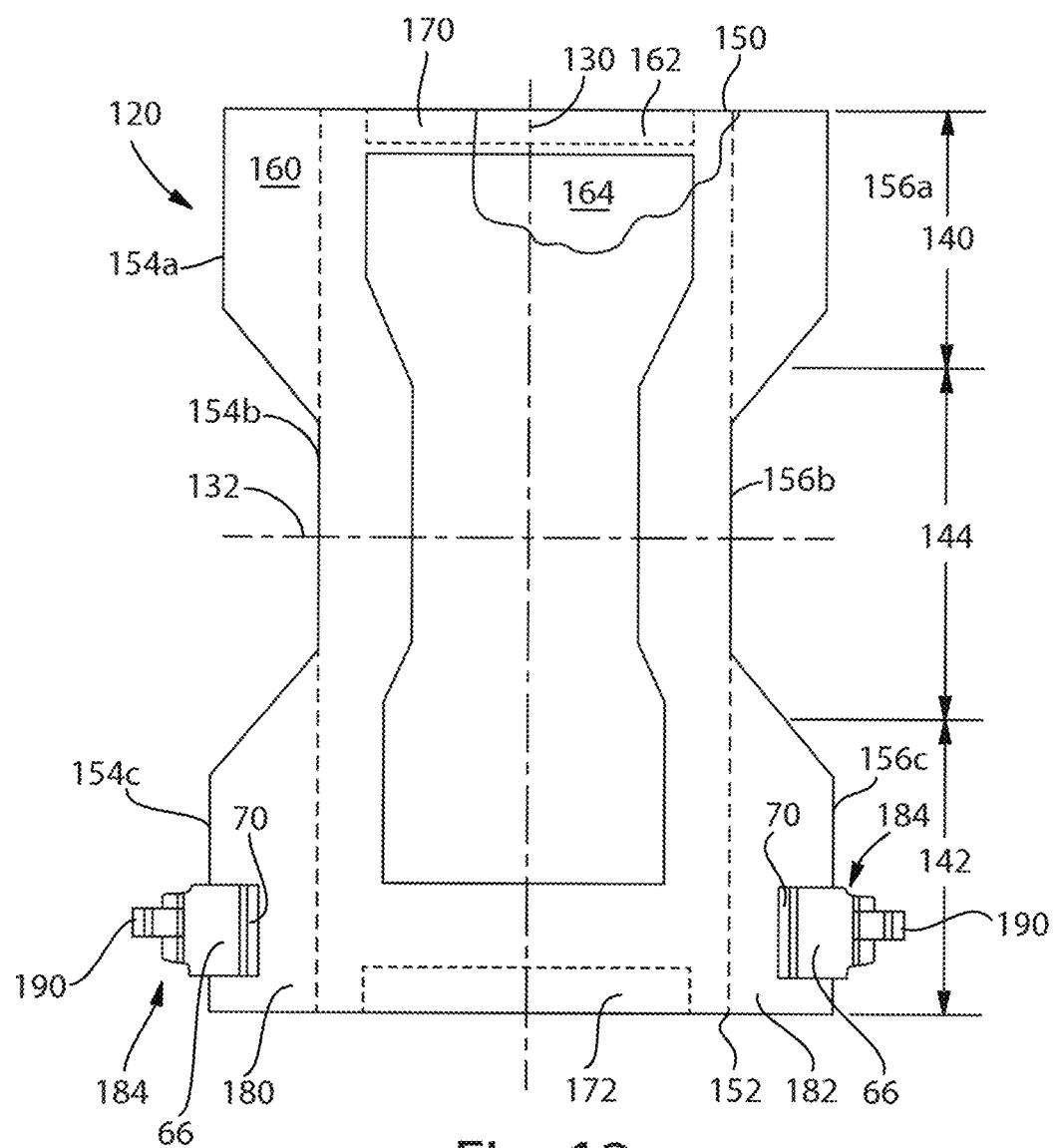
FIG. 12 is a top view of an exemplary absorbent article including sections made of a stretch laminate according to the present disclosure, with a section of a topsheet removed to expose an underlying absorbent core.

FIG. 12 is a top view of an exemplary disposable absorbent article 120 in its flat, uncontracted state (i.e., without elastic-induced contraction). Portions of disposable absorbent article 120 have been cut away to more clearly show the underlying structure of the article. As illustrated, the portion of disposable absorbent article 120 that contacts the wearer faces the viewer (i.e., showing the interior or inner side of the article). Disposable absorbent article 120 has a longitudinal axis 130 and a transverse axis 132.

One end portion of disposable absorbent article 120 is configured as a first waist region 140 of the article. The opposite end portion is configured as a second waist region 142 of disposable absorbent article 120. Waist regions 140 and 142 generally comprise those portions of disposable absorbent article 120 which, when worn, encircle the waist of the wearer. Waist regions 140 and 142 may include elastic elements such that they gather about the waist of the wearer to provide improved fit and containment. An intermediate portion of disposable absorbent article 120 is configured as a crotch region 144, which extends longitudinally between first and second waist regions 140, 142. Crotch region 144 is that portion of disposable absorbent article 120 which, when the article is worn, is generally positioned between the legs of the wearer.

Disposable absorbent article 120 has a laterally extending first waist edge 150 in first waist region 140 and a longitudinally opposing and laterally extending second waist edge 152 in second waist region 142. Disposable absorbent article 120 has a first side edge 154 and a laterally opposing second side edge 156, both side edges extending longitudinally between first waist edge 150 and second waist edge 152. The portion of first side edge 154 in first waist region 140 is designated 154a, the portion in crotch region 144 is designated 154b, and the portion in second waist region 142 is designated 154c. The corresponding portions of second side edge 156 are designated 156a, 156b, and 156c, respectively.

Disposable absorbent article 120 preferably comprises a water-permeable topsheet 160, a water-impermeable backsheet 162, and an absorbent assembly or core 164, which may be disposed between the topsheet and the backsheet, with the topsheet attached to the backsheet. Topsheet 160 may be fully or partially elasticized or may be foreshortened. Exemplary structures including elasticized or foreshortened topsheets are described in greater detail in U.S. Pat. Nos. 4,892,536; 4,990,147; 5,037,416; and 5,269,775, among others.

Disposable absorbent article 120 may include at least one elastic waist feature 170 that helps to provide improved fit and containment. Elastic waist feature 170 may be intended to elastically expand and contract to dynamically fit the wearer's waist. Elastic waist feature 170 may extend at least longitudinally outwardly from at least one waist edge (e.g., edge 150) of absorbent article 150 and generally forms at least a portion of the waist region (e.g., region 140) of absorbent article 120. Diapers are often constructed so as to have two elastic waist features 170, 172, one (170) positioned in first waist region 140 and one (172) positioned in second waist region 142. Further, elastic waist feature 170, 172 may be made of stretch laminate 20 attached or joined to backsheet 162. Alternatively, elastic waist feature 170, 172 may be constructed as an extension of other elements of the absorbent article, such as topsheet 160, backsheet 162, or both the topsheet and the backsheet (e.g., topsheet 160 or backsheet 162 defines one of the cover layers 24, 26 of stretch laminate 20). Other elastic waist feature constructions are described in U.S. Pat. Nos. 4,515,595; 4,710,189; 5,151,092; and 5,221,274.

Disposable absorbent article 120 may include side panels 180, 182 attached to backsheet 162. In some embodiments, side panels 180, 182 may include ear panels 184. As detailed above, one or more of the side panels 180, 182, or particular portions of such side panels such as ear panels 184, may be elastically elongatable panels made from stretch laminate 20. This construction may provide a more comfortable and contouring fit by initially conformably fitting disposable absorbent article 120 to the wearer, and sustaining this fit throughout the time of wear well past when the article has been loaded with body wastes, insofar as elasticized side panels 180, 182 allow the sides of the article to expand and contract. Side panels 180, 182 may also provide more effective application of disposable absorbent article 120 because even if the caretaker pulls one elasticized side panel 180 farther than the other (182) during application, the absorbent article 120 will "self-adjust" during wear. While disposable absorbent article 120 preferably has side panels 180, 182 disposed in second waist region 142, the article may be provided with side panels disposed in first waist region 140, or in both front waist region 140 and second waist region 142.

Disposable absorbent article 120 may include fasteners 190 disposed on ear panels 184. Fasteners 190 may also be disposed directly on the interior of the article in second waist region 142 adjacent to portion 154c of first side edge 154 and adjacent to portion 156c of second side edge 156. Fasteners 190 may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive that releasably adheres to the mating surface. In fact, the fasteners may include tape tabs, hook and loop fastening components, interlocking fasteners such as tabs & slots, buckles, buttons, snaps, and/or hermaphroditic fastening components. Exemplary surface fastening systems are disclosed in U.S. Pat. Nos. 3,848,594; 4,662,875; 4,846,815; 4,894,060; 4,946,527; 5,151,092; and 5,221,274, while an exemplary interlocking fastening system is disclosed in U.S. Pat. No. 6,432,098. The fastening system may also include primary and secondary fastening systems, as disclosed in U.S. Pat. No. 4,699,622. Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428, 526.

Still other variations are also possible. For example, fasteners 190 may be disposed on the interior of disposable absorbent article 120 in first waist region 140 such that first waist region 140 overlaps second waist region 142 when they are fastened together. As another example, fasteners 190 may be disposed on the exterior of disposable absorbent article 120 rather than on the interior. As a further example, fasteners 190 may be used with a specific mating fastener surface particularly suited for cooperation with the fasteners (e.g., a loop layer that works with a hook fastener, or a layer particularly treated to provide a suitable contacting surface for a specific adhesive).

Figure 13:
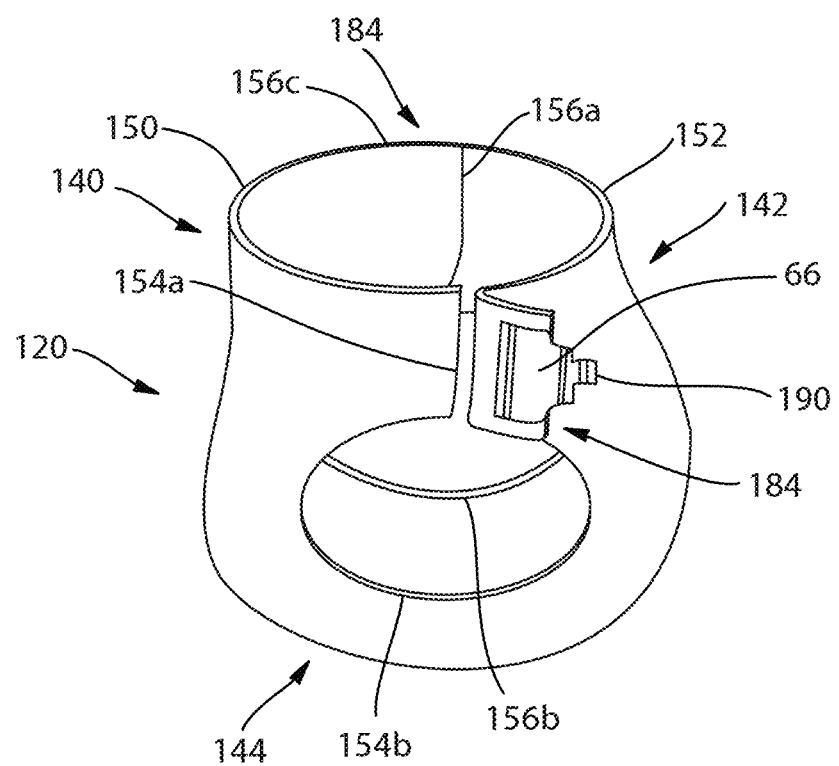
FIG. 13 is a perspective view of the absorbent article of FIG. 12 shown in its contracted state, i.e., with the contraction induced by elastic members.

FIG. 13 depicts disposable absorbent article 120 configured to as it would be during use. Portion 154c of side edge 154 is shown in an open condition, such as prior to closing and fastening or after being reopened. Portion 156c of opposing side edge 156 is shown fastened. Second waist region 142 overlaps first waist region 140 when they are fastened together. Alternatively, disposable absorbent article 120 may also include permanent or refastenable side seams that can be used to fasten the waist regions together. According to one exemplary embodiment, the side seams may include fasteners (or another form of attachment) that can be used to configure the article like a pair of pull-on training pants or disposable pants.

Figure 14:
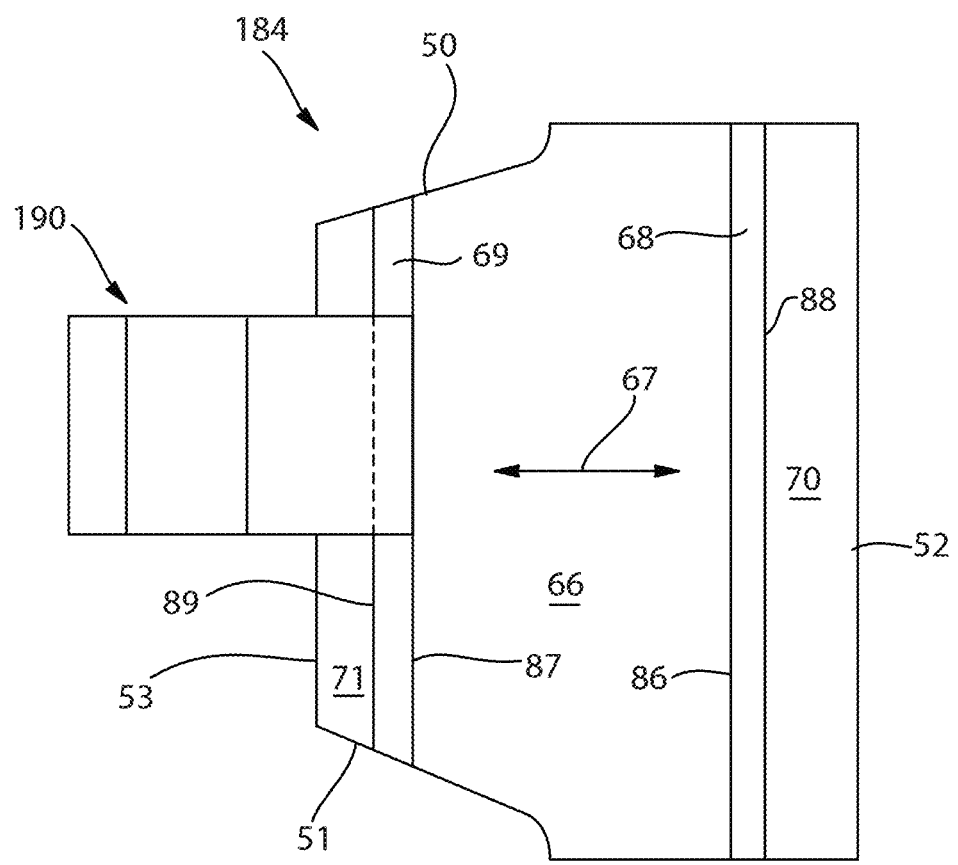
FIG. 14 is a top view of an exemplary ear panel fabricated from a stretch laminate according to the present disclosure.

FIG. 14 illustrates a top view of an exemplary embodiment of ear panel 184 that is fabricated out of stretch laminate 20 that has been mechanically activated. Ear panel 184 has a first longitudinally outermost lateral edge 50, a second longitudinally outermost lateral edge 51, an inboard end 52 and an outboard end 53. A stretch zone 66 of stretch laminate 20 is mechanically activated and is elastically extensible along a stretch direction 67. Stretch zone 66 may extend between inboard stretch zone extent 86 and outboard stretch zone extent 87. Stretch zone extents 86, 87 may fall along inboard and outboard lines at which a region of mechanical activation is bounded. Bordering stretch zone 66 are anchoring zones 68, 69. Anchoring zone 68 may extend between inboard stretch zone extent 86 and inboard anchoring zone extent 88. Anchoring zone 69 may extend between outboard stretch zone extent 87 and outboard anchoring zone extent 89. Anchoring zones 68, 69 of stretch laminate 20 are not mechanically activated.

Fastener 190 may be integrally formed with ear panel 184, or formed from a separate material. In embodiments where fastener 190 is formed from a separate material, the fastener may be attached to the ear panel 184 at a fastener attachment zone 71, which may be bounded by outboard end 53 and outboard stretch zone extent 87. The fastener may be attached to ear panel 184 in any suitable manner, including, but not limited to, continuous or intermittent adhesive bonding, compression bonding, heat bonding, ultrasonic bonding, combinations thereof, etc. Ear panel 184 may be integrally formed with a side panel, or formed from a separate material. In embodiments where ear panel 184 is formed from a separate material, the ear panel may be attached to the side panel at an ear panel attachment zone 70, which may be bounded by inboard end 52 and inboard stretch zone extent 86. Ear panel 184 may be attached to a side panel in any suitable manner, including, but not limited to, continuous or intermittent adhesive bonding, compression bonding, heat bonding, ultrasonic bonding, combinations thereof, etc.

As further detailed in the STRETCH LAMINATE FABRICATION METHOD below, stretch laminate 20 is mechanically activated by stretching the laminate transversely in relation to the direction of the web. The technique for forming such a stretch laminate is generally referred to as "zero strain" stretch laminate formation. Examples of zero strain stretch laminate formations and the resulting stretch laminates are described in U.S. Pat. Nos. 4,116,892; 4,834,741; 5,143,679; 5,156,793; 5,167,897; 5,422,172; and 5,518,801. In the particular zero strain stretch laminate formation detailed herein, stretch laminate 20 may be guided through a nip between two profile rollers, each roller including at least two disk packets having a plurality of intermeshing disks that are situated on an axis. This process is also commonly referred to as a "ring rolling" process. Stretch laminate 20 is transversely stretched in places by the intermeshing disk packets. The region in which stretch laminate 20 is stretched by the intermeshing disk packets is referred to as stretch zone 66. In the roller sections between and/or outside the disk packets, the profile rollers form a gap, through which stretch laminate 20 is guided though essentially without transverse stretching. The regions in which stretch laminate 20 are not stretched by the intermeshing disk packets are referred to as anchoring zones 68, 69.

In stretch zone 66, the fibers of cover layers 24, 26 are modified and irreversibly stretched due to fiber tears and rearrangements. However, because stretch laminate 20 includes elastomeric film 22 that has been pre-activated, the elastomeric film between the cover layers is not further substantially stretched during the mechanical activation process (i.e., a substantial amount of set is not added to the film during activation of the stretch laminate). In other words, elastomeric film 22 has substantially the same transverse width before and after mechanical activation of stretch laminate 20. This is because a significant portion (or the entire) non-elastic fraction of elastomeric film 22 (i.e., the set value) has already been removed in the pre-activation process. Accordingly, the expansion property of the fabricated stretch laminate 20 is improved in stretch zones 66 in the cross-direction (i.e., transverse in relation to the longitudinal web direction) due to mechanical activation. Following activation, when applying minimal force, stretch laminate 20 is easily expandable in the cross-direction.

Thus, in mechanically activated stretch laminate 20 (as used to fabricate ear panel 184 and other absorbent article parts), elastomeric film 22 is activated in both stretch zone 66 and anchoring zones 68, 69. In previous stretch laminates that did not include a pre-activated elastomeric film, the mechanically activated stretch laminate would include an elastomeric film that was activated in stretch zone 66, but not activated in anchoring zones 68, 69. Accordingly, the portion of the elastomeric film that was located in the anchoring zones did not contain a plurality of wrinkles. Also, when the viewed from the top, the portion of the elastomeric film that was located in the anchoring zones did not include a plurality of activation stripes. Further, in previous stretch laminates that did not include a pre-activated elastomeric film, the adhesive bonding the elastomeric film to the cover layers was in contact with a non-wrinkled surface on the surface of the film located in both stretch zone 66 and anchoring zones 68, 69 during fabrication. In stretch laminate 20 described herein, adhesive 30, 32 that bonds elastomeric film 22 to cover layers 24, 26 is in contact with a textured surface having a plurality of wrinkles on the surface of the film located in both stretch zone 66 and anchoring zones 68, 69 during fabrication, providing for increased bond strength between the film and the cover layers.

Stretch Laminate Fabrication Method

Figure 15:
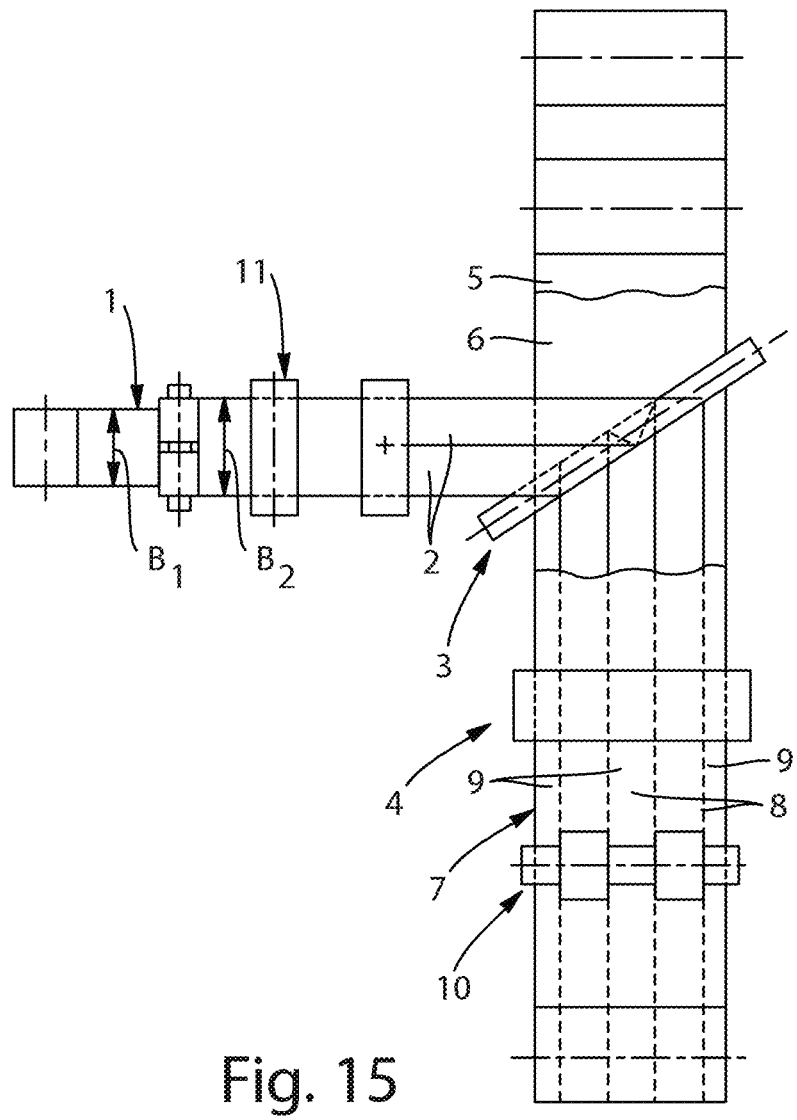
FIG. 15 is a schematic illustration of a continuous process for making a stretch laminate according to the present disclosure.

The schematic illustration of FIG. 15 details an exemplary embodiment of a method for fabricating the stretch laminates detailed herein. The method includes providing and pre-activating an elastomeric film 1 (as detailed in the STRETCH LAMINATE section above). Elastomeric film 1 is mechanically pre-activated by stretching the film transverse to its web direction by more than 50%. In some embodiments, an expansion by about 100% to about 500% occurs in relation to the starting width of elastomeric film 1. The term "stretching" is to point to the fact that the expansion of elastomeric film 1 is not completely reversible and that a non-elastic fraction results in the film having a larger width following retraction (i.e., reverse expansion). After expansion, elastomeric film 1 retracts and has a width $B_2$ that is larger by about 10% to about 30% in relation to a starting width $B_1$ of the film. Accordingly, elastomeric film 1 has a set of about 10% to about 30% resulting from the pre-activation process.

For the pre-activation process, elastomeric film 1 may be guided through a system of intermeshing profile rollers, each roller including disk packets having a plurality of intermeshing disks that are situated on an axis (i.e., a ring rolling process). Elastomeric film 1 is transversely stretched by the intermeshing disk packets. The stretching may be uniform or varied over the width of the film. The pre-activation process can be carried out at varying pitch and or varying depths of engagement. The pre-activation process can also be carried out in machine direction, or in any other direction. The pre-activation of elastomeric film 1 has a positive effect on the stretching force profile and helps allow for an easy stretching action of the fabricated stretch laminate over a large expansion area. Further, the recovery of the stretch laminate can also be improved by pre-activating elastomeric film 1. The recovery is the ability of a stretch laminate to return to original size after it has been stretched to its expansion limit. The increased recovery of elastomeric film 1 after the pre-activation process is due to the removal of an amount of set from the film.

After preactivation, but before cutting elastomeric film 1 into film strips 2, the film may optionally be printed in a printing station 11 with an image or motif that may show through the cover layers of the stretch laminate. Any known continuous printing methods can be used for printing the elastomeric film 1. Non-limiting exemplary printing methods include digital printing, inkjet printing, and rotary printing methods, in particular, flexography. As a non-limiting example, the printed image or motif can be a striped motif made of parallel colored stripes that extend in the web's longitudinal direction of elastomeric film 1.

The pre-activated, and optionally printed, film is then cut into film strips 2. The film strips 2 are guided across redirecting means 3 and supplied to laminating means 4 as parallel strips. Film strips 2 are then laminated in laminating means 4 between cover layers 5, 6 (as detailed in the STRETCH LAMINATE section above), which are supplied above and below the film strips. Film strips 2 and cover layers 5, 6 may be glued together or connected to each other by thermal means to form composite material 7 (i.e., an embodiment of the stretch laminate materials detailed herein). As illustrated in FIG. 15, film strips 2 are laminated at a distance relative to each other between cover layers 5, 6. Cover layers 5, 6 are therefore directly connected to each other in the regions between film strips 2. Accordingly, elastic regions 8, as well as non-elastic regions 9, are created in composite material 7. The distance between film strips 2 can be adjusted by positioning the redirecting means. It is also contemplated that reinforcement strips may be laminated between film strips 2 to reinforce non-elastic regions 9 between the film strips.

Composite material 7 is then supplied to an activation means 10 in which the composite material is stretched at portions of elastic regions 8 transversely in relation to the direction of the web. For the stretching, composite material 7 may be guided through a nip between two profile rollers, each roller including at least two disk packets having a plurality of intermeshing disks that are situated on an axis. Composite material 7 is transversely stretched in places by the intermeshing disk packets. The regions in which composite 7 is stretched by the intermeshing disk packets are referred to as stretch zones. In the roller sections between and/or outside the disk packets, the profile rollers form a gap, through which composite 7 is guided though essentially without transverse stretching. The regions in which composite 7 is not stretched by the intermeshing disk packets are referred to as anchoring zones. In the stretch zones, the fibers of cover layers 5, 6 are modified and irreversibly stretched due to fiber tears and rearrangements. Accordingly, the expansion property of composite material 7 is improved in the stretch zones in the cross direction (i.e., transverse in relation to the longitudinal web direction). Following activation, when applying minimal force, composite material 7 is easily expandable in the cross direction to an expansion limit that is preset by the stretching of activation means 10.

When traditional nonwovens are utilized as the cover layers, any pre-activation of elastomeric film 1 cannot replace but can only supplement the mechanical activation of composite material 7. Accordingly, even when elastomeric film 1 is pre-activated, it is still necessary for composite material 7 to be stretched transversely relative to the direction of the web in the regions that are to be rendered elastic via laminated elastomeric film strips (i.e., stretch zones). However, there may be some embodiments of composite material 7 that use extensible nonwovens as the cover layers, and therefore it may not be necessary to activate the composite material.

In fabrication of the printed stretch laminate embodiments that are disclosed herein, elastomeric film 1 is printed with an image or motif, which shows through at least one of the cover layers 5, 6 of composite material 7. Due to the fact that elastomeric film 1 is provided with the imprint, correct alignment of the printed motif relative to the elastic region of composite material 7 is always ensured. In addition, when stretching composite material 7, the printed image is evenly and reversibly stretched along with it. Furthermore, the printed motif may show through on the front side as well as on the back side of composite material 7, such that the composite material is optically equally attractive on the front as well as the back side thereof.

Test Methods

T-Peel Test

For each of the sample preparations described below, the adherent and adherend must be handled with care to avoid contact with hands, skin, or other contaminating surfaces. Clean sheets of untreated paper may be used to protect the surfaces of the adherent and adherend during the sample preparation. This method is used to determine the T-Peel strength of the bond formed between an adherent and an adherend with adhesive in between.

Sample Preparation—The sample preparation for the T-peel test will vary based on whether the material is available as a discrete web or is incorporated in a product.

Figure 16:
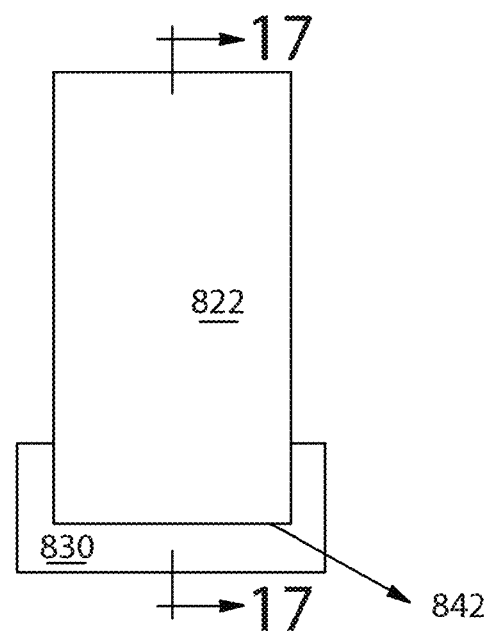
FIG. 16 is a schematic illustration of a top view of a T-Peel test sample.
Figure 17:
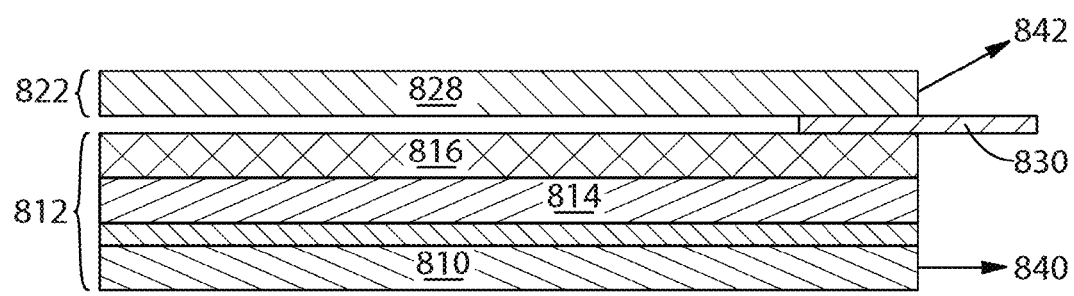
FIG. 17 is a schematic illustration of a cross-sectional view of the T-Peel sample of FIG. 16, taken along line 17-17.

For Materials as a Discrete Web: FIGS. 16 and 17 illustrate a bonded sample formed according to the directions provided below. FIG. 17 is a cross-sectional view taken along sectional line 17-17 of FIG. 16.

For a receiving sample 812 having a proximal edge 840, an adherend 814 (i.e., film either pre-activated or unactivated) is resized using cutting dies to create rectangular receiving samples with the dimensions of 7.62 cm (3") wide in material cross direction (perpendicular to machine direction) and 20 cm (7.9") long in material machine direction. The material that forms the adherend 814 is to be free of pleats (i.e., areas in which the adherend 814 folds or creases onto itself). The adherend 814 is elastomeric, hence the receiving sample is backed with like sized piece of poly (ethylene terephthalate) film (PET film, 200 gauge, X-Clear) 810 using double sided tape (such as FT 239 available from Avery Denninson Corp., Painesville, Ohio or 9589 available from 3M, St. Paul, Minn.). The bonded sample is rolled with a 4.5 pound (2 kg) HR-100 ASTM 80 shore rubber-faced roller (2" wide), rolled one time over the entire bonded area. The bonded sample is to be free of pleats (i.e., areas in which the bonded sample folds or creases onto itself).

Adhesive H2861 available from Fuller is sprayed in spiral pattern at 7 gsm basis weight on release paper (such as a double sided silicone coated paper available as supplier code HV100-473/473 from Fox River Associates, LLC., Geneva, Ill.). Spirals are sprayed in ~12 mm diameter at frequency of 3 spirals per mm in machine direction length, and adjacent to each other with minimum (<1 mm) overlap. A sheet of such glue sprayed release paper in dimension of 7.62 cm in machine direction and 20 cm in cross direction is cut. The cut sample with the adhesive side facing the adherend 814 is applied on top of the adherend 814, which is backed with PET film 810. The bonded sample is rolled with a 4.5 pound (2 kg) HR-100 ASTM 80 shore rubber-faced roller (1.75" wide), rolled one time across sample width. The release paper from the bonded sample is then pulled off, leaving glue layer 816 on adherend 814. Such created receiving sample 812 is used for bonding with engaging sample 822 described below. It should be appreciated that the receiving sample 812 can be created with larger sized materials and then resized to 7.62 cm×20 cm.

For the engaging sample 822, a 7.62 cm (3") wide×20 cm (7.9") long piece of an adherent 828, which is poly(ethylene terephthalate) film, is used. The adherent 828 is to be free of pleats (i.e., areas in which the adherent 828 folds or creases onto itself).

The engaging sample 822 is bonded to the receiving sample 812 with the adhesive on the bonding surface. Bonding is to be performed on a flat, clean, rigid surface such as a countertop. The engaging sample 822 is applied to the adhesive layer 816 on receiving sample 812 so as to avoid pleats in the sample. The adhesive layer 816 is centered on the adherent 828 with the longitudinal edges of the adherent 828 being substantially parallel to the longitudinal edges of the adherend 814 and adhesive layer 816. The proximal edge 840 of the receiving sample 812 is aligned with the proximal edge 842 of the engaging sample 822. The receiving sample 812 and engaging sample 822 should each extend at least 25 millimeters beyond the bonded portion of the samples such that the proximal edge 840 of the receiving sample 812 and the proximal edge 842 of the engaging sample 822 can be easily placed in the test instrument's grips. A small piece of release paper 830 (such as a double sided silicone coated paper available as supplier code HV00-473/473 from Fox River Associates, LLC., Geneva, Ill.) is placed between the adhesive layer 816 (adjacent the proximal edge 840) and the adherent 828 (adjacent the proximal edge 842). The release paper 830 is inserted a few millimeters between the 816 and the 828 layers (i.e., no more than 10% of the total bonded length). The bonded sample is rolled with a 11 lb steel faced roller that is 2.25" wide (4983 GR, RDL-0960-1, J-2004). Two full strokes (i.e., back and forth) are applied across the sample at a speed of approximately 10 mm/sec. Strokes are repeated over the remaining width of the sample, since width of the rubber (2.25") is less than the width of the sample (3"). The bonded area should be approximately 7.62 cm (3") wide by 20 cm (7.9") long (i.e., the same area as the engaging sample).

For the T-Peel test, a 2.54 cm (1") wide by 20 cm (7.9") long sample is cut from the bonded sample using die cut. This sample is then peeled using the method described below.

A skilled artisan should recognize that bonded specimens of other dimensions may be used in the T-Peel Method. The dimensions of the receiving and engaging members may vary from those listed above; however, the effective bonding area should be used to normalize the resultant T-Peel force recorded per inch of bonded width (i.e., the bonded width being the width of the bonded area measured substantially parallel to the grip width once the sample is mounted in the tensile tester).

Materials Incorporated in a Product: Materials that are pre-bonded in a product are taken as a prepared sample. To perform the T-peel test, the bonded material is cut from the product, if possible. However, if the adherend (wrinkled film in this case), and/or adherent are joined to other materials in a face-to-face configuration, the face-to-face configuration between the adherend and the other material or adherent and the other material should be maintained. Removal of the materials from the product should be done to preserve the integrity of the materials (e.g., adherend and adherent should not be permanently deformed or should not be debonded from each other). Before loading the samples for T-peel test, the receiving and engaging surfaces should be separated approximately 1-5 mm to initiate the peeling. The portion of the sample including the adherend is the receiving sample 812, and the portion of the sample including the adherent is the engaging sample 822. The receiving sample 812 and engaging sample 822 should each extend at least 25 millimeters beyond the bonded portion of the samples such that the proximal edge 840 of the receiving sample 812 and the proximal edge 842 of the engaging sample 822 can be easily placed in the test instrument's grips. The T-peel test should be performed on the bonded materials as described in the method below. A skilled artisan should recognize that peel angle can affect the peel force. During peeling, the peel angle should be maintained around 180 degrees (i.e., adherent and adherend pulled directly away from each other). Furthermore, if the adherent or adherend are elastomeric, the adherent or adherend must be backed with a similar sized sheet of 2 mil (0.05 mm) PET film in order to prevent stretching of the tested substrate.

Test Conditions—The T-Peel test method is performed in a controlled room at 22° C.+/− 2° C. and RH 50% +/−10%. Suitable instruments for this test include tensile testers commercially available from Instron Engineering Corp., Canton, Mass. (e.g. Instron 5564) or from MTS Systems Corp., Eden Prairie, Minn. (e.g. Alliance RT/1 or Sintech 1/S). The following procedure illustrates the measurement when using the Instron 5564. The instrument is interfaced with a computer loaded with the Instron® Merlin™ Material Testing Software which controls the testing parameters, performs data acquisition and calculation, and provides graphs and data reports. The instrument is configured with a data acquisition speed of 50 Hz. Any resulting graphs are plotted using the Average Value (integral) setting on the instrument. A load cell is selected so that the forces to be measured will be between 10% and 90% of the capacity of the load cell or the load range used (e.g., typically, a 10N to 100N load cell). The instrument is calibrated to an accuracy of at least 0.1% according to the manufacturer's instructions. The instrument has two grips: a stationary grip and a movable grip. The grips used are wider than the sample; typically, 2 inch (5.08 cm) wide grips are used. The grips are air-actuated grips and designed to concentrate the entire gripping force along a plane perpendicular to the direction of testing stress. The distance between the lines of the gripping force (i.e., gauge length) is set to 1" (2.54 cm). The load reading on the instrument is zeroed to account for the mass of the fixture and grips. The bonded sample is mounted so that the proximal edge 840 of the receiving sample 812 is in the movable grip and the proximal edge 842 of the engaging sample 822 is in the stationary grip. The bonded sample is mounted such that there is a minimum amount of slack in the receiving sample 812 or engaging sample 822 between the grips. The specimen is mounted into the grips in a manner such that there is no slack and the load measured is between 0.00 Newton and 0.02.

The receiving sample 812 is separated from the engaging sample 822 using a crosshead speed of 12 inches/min (305 mm/min). An average load is calculated as the average load between about 1" (about 25 mm) and about 6.26" (about 160 mm) displacement. For samples that do not meet the dimensions provided in the Sample Preparation, the average load is calculated from the loads acquired from the crosshead extension between about 25% to about 87.5% of the sample length. For example, if the sample is 4" long, the average load is calculated between about 1 inches (2.54 cm) to 3.5" length of the sample. The average load is normalized as follows: normalized load (N/cm)=average load÷initial bond width in centimeters. For 1" wide sample, average load is divided by 2.54 cm to get normalized load. N=at least 3 samples evaluated to get good average peel.

Hysteresis (% Set) Test:

This method is used to determine properties of elastomers, including the form of flat films, which may correlate with the growth in product dimension experienced during the processing of the product containing the elastomeric composition. The hysteresis test method is performed at room temperature (22-25° C.). The material to be tested is cut into a substantially rectilinear shape in the material's cross direction. Sample dimensions should be selected to achieve the required strain with forces appropriate for the instrument. Suitable sample dimensions are approximately 25.4 mm wide (in the direction perpendicular to stretching, machine direction) by approximately 76.2 mm long (in the direction of stretching, cross direction). Suitable instruments for this test include tensile testers from MTS Systems Corp., Eden Prairie, Minn. (e.g. Alliance RT/1 or Sintech 1/S) or from Instron Engineering Corp., Canton, Mass. For either the Alliance RT/1 or Sintech 1/S instruments listed above.

The following procedure illustrates the measurement when using the above sample dimensions and either an Alliance RT/1 or Sintech 1/S. The instrument is interfaced with a computer. TestWorks 4® software controls the testing parameters, performs data acquisition and calculation, and provides graphs and data reports.

The grips used for the test are wider than the sample. 2 inch (5.08 cm) wide grips may be used. The grips are air actuated grips designed to concentrate the entire gripping force along a single line perpendicular to the direction of testing stress having one flat surface and an opposing face from which protrudes a half round (radius=6 mm) (Part number: 56-163-827 from MTS Systems Corp.) to minimize slippage of the sample.

The load cell is selected so that the forces measured will be between 10% and 90% of the capacity of the load cell or the load range used. A 25 Newton load cell may be used. The fixtures and grips are installed. The instrument is calibrated according to the manufacturer's instructions. The distance between the lines of gripping force (gauge length) is 1 inch (25.4 mm), which is measured with a steel ruler held beside the grips, unless specified otherwise. The load reading on the instrument is zeroed to account for the mass of the fixture and grips. The mass, thickness, and basis weight of the specimen are measured before testing. The specimen is mounted into the grips in a manner such that there is no slack and the load measured is between 0.00 Newton and 0.02 Newton, unless specified otherwise. The instrument is located in a temperature-controlled room for measurements performed at 22° C.

The hysteresis test method for film samples involves the following steps (all strains are engineering strains):
(1) Strain the sample to 500% strain at a constant crosshead speed of 10 inches per minute (25.4 cm per minute) with no hold.
(2) Reduce strain to 0% strain (i.e., return grips to original gauge length of 1 inch) at a constant crosshead speed of 10 inches per minute (25.4 cm per minute) with no hold.
(3) Hold sample for 1 minute at 0% strain
(4) Pull the sample to 0.05 N force at a constant crosshead speed of 0.51 inches per minute (13 mm per minute) and return to zero strain at the same crosshead speed to measure the set in the material. The set or the growth in the sample changes the gauge length. The method adds the extension up to the 0.05 N force to original 25.4 mm gauge length to calculate New Gauge length.
(5) Strain the sample to 200% strain based on new gauge length at a constant crosshead speed of 10 inches per minute (25.4 cm per minute).
(6) Hold at 200% strain for 30 seconds.
(7) Go to 0% strain at a constant crosshead speed 10 inches per minute (25.4 cm per minute).

The method reports New Gauge length for each sample, which is the new length of the sample after straining to 500% and one minute of consequent hold time at 0% strain. The New Gauge length is used to calculate % set in the material as follow.

% Set=100*(New Gauge length−original gauge length)/original gauge length

EXAMPLES

T-Peel Examples

Example 1

Unactivated film KC 6282.810 available from Mondi GmbH, Gronau in 40 μm was used as adherend. The film is made of elastic polyolefin resin using a blown film extrusion process. It is a three layer film with elastic polyolefin film in core, while the skin on each side is made of plastic polyolefin. This film was bonded to PET film, using double sided tape. The T-peel sample was created using H2861 glue, and PET as described in the method above.

Example 2

The film used in Example 1 was pre-activated using the incremental stretching process as described in U.S. Pat. Nos. 5,143,679, 5,156,793 and U.S. Pat. No. 5,167,897 patents issued to Weber et. al. It was pre-activated in cross-direction using 0.150" pitch roll at 6 mm Depth of Engagement. This created wrinkles in the film skins, as described and illustrated herein. The pre-activated film was used as adherend to create a T-Peel sample as described in the method above. The sample is mounted in a way that it is peeled in machine direction (i.e., a direction parallel to the activation lines).

Figure 18:
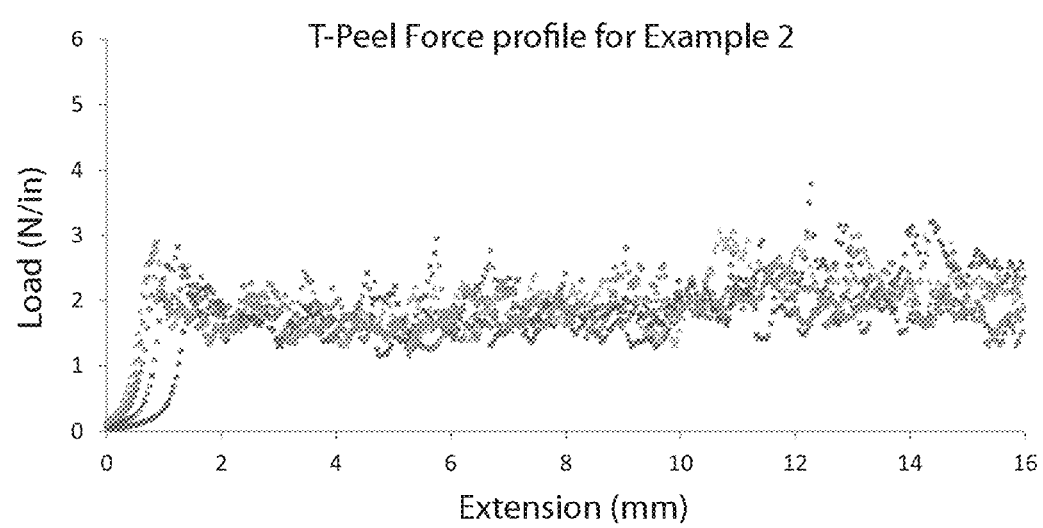
FIG. 18 is an exemplary chart plotting T-Peel curves generated using the T-Peel test method. The exemplary chart plots T-Peel data for Example 2.

Both samples (i.e., Example 1 and 2) were T-Peeled as per the method described above. When peeled, the adhesive, which was applied on adherend, peeled off completely from it and transferred to adherent PET. This was true for both samples. This indicated that T-Peel force was indicative of adhesive failure between adhesive and adherend, and not between adhesive and adherent PET. FIG. 18 shows the T-Peel data curves for samples of Example 2. The difference in the bonding force was evident in the T-Peel force data between two samples shown in Table 1 below.

TABLE 1

T-Peel force data for various samples of examples 1 and 2.

|  | 1 | 2 | 3 | 4 | 5 | Average (N/cm) | Standard Deviation (N/cm) |
|---|---|---|---|---|---|---|---|
| Example 1 | 0.7 | 0.65 | 0.66 |  |  | 0.67 | 0.03 |
| Example 2 | 0.78 | 0.81 | 0.75 | 0.73 | 0.75 | 0.76 | 0.03 |

The pre-activated film of Example 2 showed higher bonding force compared to the un-activated film of Example 1. Even though both samples tested are 1" wide, the wrinkles in the pre-activated sample provides a larger bonding surface compared to the un-activated film. The corrugated surface on the film (wrinkles in the skin) has hills and furrows. As adhesive is pushed into the furrows during bonding step, it increases contact points and hence bonding area. The more bonding surface area translates into higher peel force. The stretch laminating process uses nipping after adhesive application to create a stronger bond. Having furrows and hills on the film surface therefore enhances the bond properties.

T-Peel is often indicator of product robustness. The product considered here requires peel force higher than 0.5 N/cm between elastic film and substrate. Good bonding between the film and substrate prevents delamination of the substrate or the film during product use. Example 2 shows almost ~14% increase in T-peel force. This increase in T-peel force allows one to utilize less adhesive with a wrinkled film (wrinkles obtained through preactivation) to achieve identical performance compared to the amount of adhesive that one would use on flat film as in Example 1. In the embodiments of the pre-activated stretch laminates contemplated herein, the peel force, as measured by the T-Peel Method described above, are about 0.5 N/cm or more, more preferably about 0.6 n/cm or more.

Hysteresis (% Set) Examples

Example 3

Styrenic block copolymer resin 21J (412-10225) available from Kuraray, was extruded to make film using Berstorff extruder ZE25. A 25.4 cm wide coat hanger cast film die is used to shape the compounded elastomer mixture into a thin film, and a film take-off unit is positioned to receive the extrudate which is collected on double sided silicone coated release paper and wound onto a cardboard roll. For generating data herein, a monolayer film is extruded at around 450 deg. F at ~35 gsm at very low speed (~10 ft/min). The film is collected from the 254 mm cast film die, and the middle 127 mm is used for sample preparation.

Example 4

Polyolefin based elastomer Vistamaxx 6102 available from Exxon Mobil was extruded to make a film using Berstorff extruder ZE25. The film was extruded using the same set-up as in Example 3. A monolayer film was extruded at around 450° F. at ~35 gsm at very low speed (~10 ft/min).

For the hysteresis analysis, both samples were cut from the middle of the film to eliminate any edge effect on the performance. Five samples for each example with dimension of 3" in Cross direction and 1" in Machine direction (extrusion direction) were cut. Mono-layer elastic films are harder to handle, and often powdered (corn starch or talc) before handling. These samples were then analyzed as per the hysteresis method described above. Although the method measured various performance parameters, Table 2 below lists the % set value for the materials

TABLE 2

% Set measured with Hysteresis method for samples of Ex. 3 and Ex. 4.

|  | 1 | 2 | 3 | 4 | 5 | Average % Set | Standard Deviation % Set |
|---|---|---|---|---|---|---|---|
| Example 3 | 21% | 21% | 21% | 22% | 20% | 21% | 1% |
| Example 4 | 56% | 53% | 55% | 58% | 55% | 55% | 2% |

A new class of polyolefin materials made out of polypropylene show elastic behavior. However, they show very high set relative to traditional elastomers made of Styrenic block copolymers. Stretch laminates made out of elastic film and non-elastic nonwovens often require mechanical activation to release elasticity. Mechanical activation is most commonly carried out in cross-direction. During activation, if the elastic film shows high set, the post-activation process becomes unstable. To handle the elongated web process often requires costly equipment and a large space. More importantly, the web elongation in cross-direction reduces the reliability and speed of the process. Styrenic block copolymer based films are commonly used in the ring-rolling process and stretch laminate making process. As shown in Table 2 for Example 3, Styrenic Block copolymer films used in such process show 20% to 25% set, at most 30% set when strained to 500% as described in the hysteresis method. On contrary, the new generation elastic polypropylene films of Example 4 show about 55% set in the material. The film or laminate web with such high set will creates web handling challenges and requires new capital. However, this can be addressed by pre-activating film. Once the set in the material is induced via pre-straining, material sees less set in the consequent activation steps. In addition, elastic polyolefin materials show better hysteresis properties after pre-activation, compared to one before pre-activation. In the embodiments of the pre-activated stretch laminates contemplated herein, the % set, as measured by the Hysteresis Method described above, are about 30% or more, and preferably about 35% or more.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference; the citation of any document is not to be construed as an admission that it is prior art with respect to the present invention. To the extent that any meaning or definition of a term in this disclosure conflicts with any meaning or definition of the term in a document incorporated by reference, the meaning or definition assigned to the term in this disclosure shall govern for this disclosure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising: i) a chassis comprising a topsheet, a backsheet, and an absorbent core disposed between the topsheet and the backsheet; and ii) at least one elastically elongatable panel joined to the chassis, wherein the elastically elongatable panel comprises a stretch laminate comprising:
   a. at least one cover layer; and
   b. a mechanically pre-activated elastomeric film attached to the cover layer, the elastomeric film having two surfaces and a skin on at least one of the surfaces;
   wherein the stretch laminate has at least one anchoring zone and at least one stretch zone, wherein the stretch zone is mechanically activated, and the anchoring zone is not mechanically activated, and wherein the stretch zone of the stretch laminate is elastically extensible along a stretch direction, and the anchoring zone of the stretch laminate is attached to the chassis or a fastener, and is not extensible along the stretch direction;
   wherein when the stretch zone is mechanically activated, fibers of the cover layer in the stretch zone are irreversibly stretched due to fiber tears and rearrangements;
   wherein the skin of the elastomeric film that is located in the anchoring zone has a plurality of wrinkles.

2. The absorbent article of claim 1, wherein the elastomeric film comprises a polyolefin elastomer.

3. The absorbent article of claim 2, wherein the polyolefin elastomer is a propylene based homopolymer or co-polymer, or ethylene based homopolymer or co-polymer selected from the group consisting of: an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene tri-block copolymer, an isotactic polypropylene block region-irregular polypropylene block isotactic polypropylene tri-block copolymer, a polyethylene random (ethylene/olefin) copolymer block copolymer, a reactor blend polypropylene, a very low density polypropylene, a metallocene polypropylene, metallocene polyethylene, and combinations thereof.

4. The absorbent article of claim 1, wherein the elastomeric film is a blown film.

5. The absorbent article of claim 1, wherein the elastomeric film is between about 20 μm and about 60 μm thick.

6. The absorbent article of claim 5, wherein the elastomeric film is about 40 μm thick.

7. The absorbent article of claim 1, wherein the skin comprises a polyolefin selected from the group consisting of: metallocene polyethylene, low density polyethylene, high density polyethylene, linear low density polyethylene, very low density polyethylene, a polypropylene homopolymer, a plastic random poly(propylene/olefin) copolymer, syndiotactic polypropylene, metallocene polypropylene, polybutene, an impact copolymer, a polyolefin way, and combinations thereof.

8. The absorbent article of claim 1, wherein the elastomeric film is attached to the cover layer with a peel force, as measured by the T-Peel Test disclosed herein, of 0.5N or more.

9. The absorbent article of claim 1, wherein the elastomeric film has a % set, as measured by the Hysteresis Test disclosed herein, of 30% or more.

10. The absorbent article of claim 1, wherein the absorbent article is a diaper.

11. An absorbent article comprising: i) a chassis comprising a topsheet, a backsheet, and an absorbent core disposed between the topsheet and the backsheet; and ii) at least one elastically elongatable panel joined to the chassis, wherein the elastically elongatable panel comprises a stretch laminate comprising:
    a. a first cover layer;
    b. a second cover layer; and
    c. a mechanically preactivated elastomeric film disposed between the first cover layer and the second cover layer, the elastomeric film having a first skin on a first surface closest to the first cover layer and a second skin on a second surface closest to the second cover layer;
    wherein the stretch laminate has at least one anchoring zone and at least one stretch zone, wherein the stretch zone is mechanically activated, and the anchoring zone is not mechanically activated, and wherein the stretch zone of the stretch laminate is elastically extensible along a stretch direction, and the anchoring zone of the stretch laminate is attached to the chassis or a fastener, and is not extensible along the stretch direction;
    wherein when the stretch zone is mechanically activated, fibers of the first cover layer and fibers of the second cover layer in the stretch zone are irreversibly stretched due to fiber tears and rearrangements;
    wherein the first skin and the second skin of the elastomeric film that are located in the anchoring zone each have a plurality of wrinkles.

12. The absorbent article of claim 11, wherein the elastomeric film comprises a polyolefin elastomer.

13. The absorbent article of claim 12, wherein the polyolefin elastomer is a propylene based homopolymer or co-polymer, or ethylene based homopolymer or co-polymer selected from the group consisting of: an elastic random poly(propylene/olefin) copolymer, an isotactic polypropylene containing stereoerrors, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene tri-block copolymer, an isotactic polypropylene block region-irregular polypropylene block isotactic polypropylene tri-block copolymer, a polyethylene random (ethylene/olefin) copolymer block copolymer, a reactor blend polypropylene, a very low density polypropylene, a metallocene polypropylene, metallocene polyethylene, and combinations thereof.

14. The absorbent article of claim 11, wherein the elastomeric film is a blown film.

15. The absorbent article of claim 11, wherein the elastomeric film is between about 20 μm and about 60 μm thick.

16. The absorbent article of claim 15, wherein the elastomeric film is about 40 μm thick.

17. The absorbent article of claim 11, wherein the first skin and second skin comprise a polyolefin selected from the group consisting of: metallocene polyethylene, low density polyethylene, high density polyethylene, linear low density polyethylene, very low density polyethylene, a polypropylene homopolymer, a plastic random poly(propylene/olefin) copolymer, syndiotactic polypropylene, metallocene polypropylene, polybutene, an impact copolymer, a polyolefin way, and combinations thereof.

18. The absorbent article of claim 11, wherein the elastomeric film is attached to the cover layer with a peel force, as measured by the T-Peel Test disclosed herein, of 0.5N or more.

19. The absorbent article of claim 11, wherein the elastomeric film has a % set, as measured by the Hysteresis Test disclosed herein, of 30% or more.

20. The absorbent article of claim 11, wherein the absorbent article is a diaper.

* * * * *